United States Patent

Heistracher et al.

[11] Patent Number: 5,885,934
[45] Date of Patent: Mar. 23, 1999

[54] SUBSTITUTED TRIAZOLINONES AS CROP PROTECTION AGENTS

[75] Inventors: Elisabeth Heistracher, Ludwigshafen; Christoph Sweder von dem Bussche-Hünnefeld, Mannheim; Gerhard Hamprecht, Weinheim; Ralf Klintz, Gruenstadt; Peter Schäfer, Ottersheim; Karl-Otto Westphalen, Speyer; Matthias Gerber, Limburgerhof; Helmut Walter, Obrigheim, all of Germany

[73] Assignee: BASF Aktiengesellschaft, Ludwigshafen, Germany

[21] Appl. No.: 793,152

[22] PCT Filed: Jun. 7, 1995

[86] PCT No.: PCT/EP95/02167

§ 371 Date: Feb. 18, 1997

§ 102(e) Date: Feb. 18, 1997

[87] PCT Pub. No.: WO96/05179

PCT Pub. Date: Feb. 22, 1996

[30] Foreign Application Priority Data

Aug. 16, 1994 [DE] Germany ............... 44 29 006.3

[51] Int. Cl.⁶ .................. A01N 43/653; C07D 249/12
[52] U.S. Cl. .................. 504/169; 504/273; 548/263.2
[58] Field of Search .................. 504/273, 169; 548/263.2

[56] References Cited

U.S. PATENT DOCUMENTS 5,125,958  6/1992  Poss ............................. 71/92
5,476,949  12/1995  Tinker et al. ..................... 504/273

FOREIGN PATENT DOCUMENTS 41 31 038  9/1991  Germany .
87/03782   7/1987  WIPO .
90/02120   3/1990  WIPO .

Primary Examiner—Patricia L. Morris
Attorney, Agent, or Firm—Keil & Weinkauf

[57] ABSTRACT

Substituted triazolinones I

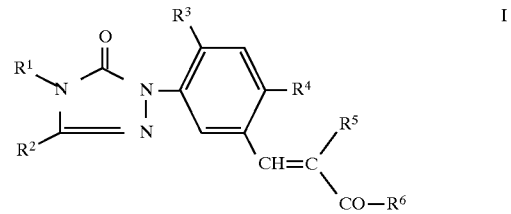

where
$R^1$ and $R^2$ are each H, $C_1-C_6$-alkyl or $C_1-C_6$-haloalkyl,
$R^3$ is H or halogen,
$R^4$ is CN, halogen, $C_1-C_6$-alkyl, $C_1-C_6$-haloalkyl, $C_1-C_6$-alkoxy or $C_1-C_6$-haloalkoxy,
$R^5$ is $NO_2$, CN or halogen,
$R^6$ is $-OR^7$, $-SR^7$, $-N(R^8)-R^9$ or $-N(R^8)-OR^{10}$,
$R^7$ is H, $C_1-C_6$-alkyl, $C_3-C_6$-alkenyl, $C_3-C_6$-alkynyl, $C_3-C_6$-cycloalkyl, $C_1-C_6$-haloalkyl, cyano-$C_1-C_6$-alkyl, $C_1-C_6$-alkoxy-$C_1-C_6$-alkyl, $C_1-C_6$-alkylthio-$C_1-C_6$-alkyl, $C_1-C_6$-alkoxycarbonyl-$C_1-C_6$-alkyl, $C_1-C_6$-alkylaminocarbonyl-$C_1-C_6$-alkyl, di-($C_1-C_6$-alkyl)aminocarbonyl-$C_1-C_6$-alkyl, $C_1-C_6$-alkoximino-$C_1-C_6$-alkyl, di-($C_1-C_6$-alkoxy)-$C_2-C_6$-alkyl, di-($C_1-C_6$-alkylthio)-$C_2-C_6$-alkyl, $C_3-C_6$-haloalkenyl or unsubstituted or substituted phenyl or benzyl,
$R^8$, $R^9$ and $R^{10}$ are each $C_1-C_6$-alkylcarbonyl or $C_1-C_6$-haloalkyl-carbonyl or each have one of the meanings stated for $R^7$,
$R^8$ and $R^9$ together form a 4- to 6-membered carbon chain in which one methylene unit may be replaced by oxygen or $C_1-C_4$-alkylimino, and the salts of I are used as herbicides or for the desiccation/defoliation of plants.

10 Claims, No Drawings

SUBSTITUTED TRIAZOLINONES AS CROP PROTECTION AGENTS

The present invention relates to novel substituted triazolinones of the general formula I

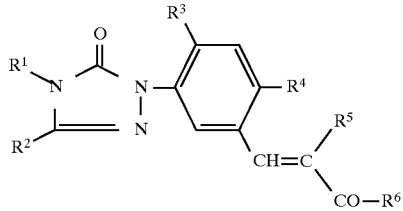

where $R^1$ is hydrogen, $C_1$–$C_6$-alkyl or $C_1$–$C_6$-haloalkyl;

$R^2$ is hydrogen, $C_1$–$C_6$-alkyl or $C_1$–$C_6$-haloalkyl;

$R^3$ is hydrogen or halogen;

$R^4$ cyano, halogen, $C_1$–$C_6$-alkyl, $C_1$–$C_6$-haloalkyl, $C_1$–$C_6$-alkoxy or $C_1$–$C_6$-haloalkoxy;

$R^5$ is nitro, cyano or halogen;

$R^6$ is —$OR^7$, —$SR^7$, —$N(R^8)$—$R^9$ or —$N(R^8)$—$OR^{10}$, $R^7$ is hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, cyano-$C_1$–$C_6$-alkyl, $C_1$–$C_6$-alkoxy-$C_1$–$C_6$-alkyl, $C_1$–$C_6$-alkylthio-$C_1$–$C_6$-alkyl, ($C_1$–$C_6$-alkoxy)carbonyl-$C_1$–$C_6$-alkyl, ($C_1$–$C_6$-alkylamino)carbonyl-$C_1$–$C_6$-alkyl, di-($C_1$–$C_6$-alkyl)aminocarbonyl-$C_1$–$C_6$-alkyl, $C_1$–$C_6$-alkyloximino-$C_1$–$C_6$-alkyl, di-($C_1$–$C_6$-alkoxy)-$C_2$–$C_6$-alkyl, di-($C_1$–$C_6$-alkylthio)-$C_2$–$C_6$-alkyl, $C_3$–$C_6$-haloalkenyl, phenyl or benzyl, where each of the phenyl rings may carry one to three radicals selected from the group consisting of cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio and ($C_1$–$C_6$-alkoxy)carbonyl;

$R^8$ and $R^9$, independently of one another, are each ($C_1$–$C_6$-alkyl)carbonyl, ($C_1$–$C_6$-haloalkyl)carbonyl or have one 45 of the meanings stated for $R^7$, or $R^8$ and $R^9$ together form a four-membered to 6-membered carbon chain in which a nonterminal methylene unit may be replaced by oxygen or $C_1$–$C_4$-alkylimino and $R^{10}$ is ($C_1$–$C_6$-alkyl)carbonyl or ($C_1$–$C_6$-haloalkyl) carbonyl or has one of the meanings stated for $R^7$, and the agriculturally useful salts of I.

The present invention furthermore relates to the use of the compounds I as herbicides and/or for the desiccation and/or defoliation of plants, herbicides and/or plant desiccants and/or defoliants which contain the compounds I as active ingredients, processes for the preparation of the compounds I and of herbicides and/or plant desiccants and/or defoliants using the compounds I and methods for controlling undesirable plant growth and/or for the desiccation and/or defoliation of plants with the compounds I.

Herbicidal triazolinones have been disclosed in WO 90/02120 and WO 87/03782. However, their action is not always completely satisfactory.

It is an object of the present invention to provide triazolinones having improved biological properties.

We have found that this object is achieved by the substituted triazolinones of the formula I. We have also found herbicides which contain the compounds I and have a very good herbicidal action. Moreover, we have found processes for the preparation of these compositions and methods for controlling undesirable plant growth of the compounds I.

The novel compounds I are furthermore suitable for the defoliation and/or desiccation of plant parts, for example, for cotton, potatoes, rape, sunflower, soybean or bush beans, in particular for cotton. In this respect, we have found compositions for the desiccation and/or defoliation of plants, processes for the preparation of these compositions and methods for the desiccation and/or defoliation of plants with the compounds I.

The organic moieties stated for the substituents $R^1$, $R^2$, $R^4$ and $R^7$ to $R^{10}$ or as radicals on phenyl rings are—as for the definition of halogen—general terms for individual lists of the individual group members. All carbon chains, ie. all alkyl, haloalkyl, cyanoalkyl, alkoxy, haloalkoxy, alkenyl, haloalkenyl, alkynyl, alkoxycarbonyl, alkylthio and haloalkylthio moieties may be straight-chain or branched, unless stated otherwise. Polyhalogenated haloalkyl, haloalkoxy, haloalkylthio and haloalkenyl radicals may carry identical or different halogen atoms.

Specific examples are:

halogen is fluorine, chlorine, bromine or iodine;

$C_1$–$C_6$-alkyl is methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

$C_1$–$C_6$-haloalkyl is chloromethyl, dichloromethyl, trichloromethyl, fluoromethyl, difluoromethyl, trifluoromethyl, chlorofluoromethyl, dichlorofluoromethyl, chlorodifluoromethyl, 2-chloroethyl, 2-fluoroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, pentafluoroethyl, 2,2,2-trichloroethyl, 3-fluoropropyl, 2-fluoropropyl, 2,2-difluoropropyl, 2,3-difluoropropyl, 3-chloropropyl, 2-chloropropyl, 2,3-dichloropropyl, 3-bromopropyl, 2-bromopropyl, 3,3,3-trichloropropyl, 3,3,3-trifluoropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_6$-alkoxy is methoxy, ethoxy, n-propoxy, 1-methylethoxy, n-butoxy, 1-methylpropoxy, 2-methylpropoxy, 1,1-dimethylethoxy, n-pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexyloxy, 1-methylpentyloxy, 2-methylpentoxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2- trimethylpropoxy, 1-ethyl-1-methylpropoxy or 1-ethyl-2-methylpropoxy;

$C_1$–$C_6$-haloalkoxy is, for example, difluoromethoxy, trifluoromethoxy, chlorodifluoromethoxy, bromodifluoromethoxy 2-fluoroethoxy, 2,2-difluoroethoxy, 2,2,2-trifluoroethoxy, 2-chloroethoxy, 2-bromoethoxy, 2-iodoethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 3-fluoropropoxy, 2-fluoropropoxy, 2,2-difluoropropoxy, 2,3-difluoropropoxy, 3-chloropropoxy, 2-chloropropoxy, 2,3-dichloropropoxy, 3-bromopropoxy, 2-bromopropoxy, 3,3,3-trichloropropoxy, 3,3,3-trifluoropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, 4-iodobutoxy, nonafluorobutoxy, 5-fluoropentyloxy, 5-chloropentyloxy, 5-bromopentyloxy, 5-iodopentyloxy, undecafluoropentyloxy, 6-fluorohexyloxy, 6-chlorohexyloxy, 6-bromohexyloxy, 6-iodohexyloxy or dodecafluorohexyloxy;

$C_1$–$C_6$-alkylcarbonyl is methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl,1,2,2-trimethylpropylcarbonyl, 1-ethyl-1-methylpropylcarbonyl or 1-ethyl-2-methylpropylcarbonyl;

$C_1$–$C_6$-haloalkylcarbonyl is, for example, chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 1-fluoropropionyl, 2-fluoropropionyl, 2,2-difluoropropionyl, 3,3,3-trifluoropropionyl, 3-chloro-3-fluoropropionyl, 3-chloro-3,3-difluoropropionyl, 3,3-dichloro-3-fluoropropionyl, trichloropropionyl or pentafluoropropionyl.

Specifically, $R^1$ to $R^{10}$ have the following meanings, in each case alone or in combination:

$R^1$ is hydrogen, $C_1$–$C_6$-alkyl or $C_1$–$C_6$-haloalkyl, preferably hydrogen, methyl or $C_1$–$C_6$-haloalkyl, in particular hydrogen, methyl, fluoromethyl, difluoromethyl, trifluoromethyl, 2-fluoroethyl, 2,2,2-trifluoroethyl or pentafluoroethyl;

$R^2$ is hydrogen, $C_1$–$C_6$-alkyl or $C_1$–$C_6$-haloalkyl, preferably hydrogen, $C_1$–$C_6$-alkyl or $C_1$–$C_4$-haloalkyl, in particular hydrogen, methyl, ethyl, n-propyl, isopropyl, n-butyl, i-butyl, sec-butyl, tert-butyl, fluoromethyl, difluoromethyl or trifluoromethyl;

$R^3$ is hydrogen or halogen;

$R^4$ is cyano, halogen, $C_1$–$C_6$-alkyl, $C_1$–$C_6$-haloalkyl, $C_1$–$C_6$-alkoxy or $C_1$–$C_6$-haloalkoxy, in particular cyano, fluorine, chlorine, bromine, methyl, trifluoromethyl, methoxy or trifluoromethoxy;

$R^5$ is nitro, cyano or halogen;

$R^7$ is hydrogen or $C_1$–$C_6$-alkyl as stated above;

$C_3$–$C_6$-alkenyl, such as prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_3$–$C_6$-Alkynyl, such as prop-1-yn-1-yl, prop-2-yn-1-yl, but-1-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, pent-2-yn-1-yl, pent-2-yn-4-yl, pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl;

$C_3$–$C_6$-cycloalkyl such as cyclopropyl, cyclobutyl, cyclopentyl and cyclohexyl;

$C_1$–$C_6$-haloalkyl as stated above;

cyano-$C_1$–$C_6$-alkyl, eg. cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl, 2-cyanomethylprop-2-yl, 1-cyanopent-1-yl, 2-cyanopent-1-yl, 3-cyanopent-1-yl, 4-cyanopent-1- yl, 5-cyanopent-1-yl, 1-cyanopent-2-yl, 2-cyanopent-2-yl, 1-cyanopent-3-yl, 2-cyanopent-3-yl, 1-cyanopent-4-yl, 2-cyanopent-4-yl, 3-cyanopent-4-yl, 1-cyano-2-ethylprop-3-yl, 1-cyanohex-1-yl, 2-cyanohex-1-yl, 3-cyanohex-1-yl, 4-cyanohex-1-yl, 5-cyanohex-1-yl, 6-cyanohex-1-yl, 1-cyanohex-2-yl, 2-cyanohex-2-yl, 1-cyanohex-3-yl, 2-cyanohex-3-yl, 1-cyanohex-4-yl, 2-cyanohex-4-yl, 3-cyanohex-4-yl, 1-cyano-2-ethylbut-3-yl, 1-cyano-2-ethylbut-4-yl or 1-cyano-2-propylprop-3-yl;

$C_l$–$C_6$-alkoxy-$C_1$–$C_6$-alkyl, eg. methoxymethyl, ethoxymethyl, n-propoxymethyl, (1-methylethoxy) methyl, n-butoxymethyl, (1-methylpropoxy)methyl, (2-methylpropoxy)methyl, (1,1-dimethylethoxy) methyl, n-pentyloxymethyl, (1-methylbutoxy) methyl, (2-methylbutoxy)methyl, (3-methylbutoxy) methyl, (2,2-dimethylpropoxy)methyl, (1-ethoxypropoxy)methyl, n-hexyloxymethyl, (1,1-dimethylpropoxy)methyl, (1,2-dimethylpropoxy) methyl, (1-methylpentyloxy)methyl, (2-methylpentyloxy)methyl, (3-methylpentyloxy) methyl, (4-methylpentyloxy)methyl, (1,1-dimethylbutoxy)methyl, (1,2-dimethylbutoxy) methyl, (1,3-dimethylbutoxy)methyl, (2,2-dimethylbutoxy)methyl, (2,3-dimethylbutoxy) methyl, (3,3-dimethylbutoxy)methyl, (1-ethylbutoxy)methyl, (1-ethyl-1-methylpropoxy) methyl, (2-ethylbutoxy)methyl, (1,1,2-trimethylpropoxy)methyl, (1,2,2-trimethylpropoxy) methyl, (1-ethyl-1-methylpropoxy)methyl, (1-ethyl-2-methylpropoxy)methyl, methoxyethyl, ethoxyethyl, n-propoxyethyl, (1-methylethoxy) ethyl, n-butoxyethyl, (1-methylpropoxy)ethyl, (2-methylpropoxy)ethyl, (1,1-dimethylethoxy)ethyl, n-pentyloxyethyl, (1-methylbutoxy)ethyl, (2-methylbutoxy)ethyl, (3-methylbutoxy)ethyl, (2,2-dimethylpropoxy)ethyl, (1-ethylpropoxy)ethyl, n-hexyloxyethyl, (1,1-dimethylpropoxy)ethyl, (1,2-dimethylpropoxy)ethyl, (1-methylpentyloxy)ethyl, (2-methylpentyloxy)ethyl, (3-methylpentyloxy) ethyl, (4-methylpentyloxy)ethyl, (1,1-dimethylbutoxy)ethyl, (1,2-dimethylbutoxy)ethyl, (1,3-dimethylbutoxy)ethyl, (2,2-dimethylbutoxy) ethyl, (2,3-dimethylbutoxy)ethyl, (3,3-dimethylbutoxy)ethyl, (1-ethylbutoxy)ethyl, (2-ethylbutoxy)ethyl, (1,1,2-trimethylpropoxy)ethyl, (1,2,2-trimethylpropoxy)ethyl, (1-ethyl-1-methylpropoxy)ethyl, (1-ethyl-2-methylpropoxy) ethyl, 2-(methoxy)propyl, 3-(methoxy)propyl or 2-(ethoxy)propyl;

$C_1$–$C_6$-alkylthio-$C_1$–$C_6$-alkyl, eg. methylthiomethyl, ethylthiomethyl, n-propylthiomethyl, (1-methylethylthio)methyl, n-butylthiomethyl, (1-methylpropylthio)methyl, (2-methylpropylthio) methyl, (1,1-dimethylethylthio)methyl, n-pentylthiomethyl, (1-methylbutylthio)methyl, (2-methylbutylthio)methyl, (3-methylbutylthio) methyl, (2,2-dimethylpropylthio)methyl, (1-ethylpropylthio)methyl, n-hexylthiomethyl, (1,1-dimethylpropylthio)methyl, (1,2-dimethylpropylthio)methyl, (1-methylpentylthio) methyl, (2-methylpentylthio)methyl, (3-methylpentylthio)methyl, (4-methylpentylthio) methyl, (1,1-dimethylbutylthio)methyl, (1,2-dimethylbutylthio)methyl,(1,3-dimethylbutylthio) methyl, (2,2-dimethylbutylthio)methyl, (2,3-dimethylbutylthio)methyl, (3,3-dimethylbutylthio) methyl, (1-ethylbutylthio)methyl, (2-ethylbutylthio) methyl, (1,1,2-trimethylpropylthio)methyl, (1,2,2-trimethylpropylthio)methyl, (1-ethyl-1-methylpropylthio)methyl, (1-ethyl-2-methylpropylthio)methyl, methylthioethyl, ethylthioethyl, n-propylthioethyl, (1-methylethylthio)ethyl, n-butylthioethyl, (1-methylpropylthio)ethyl, (2-methylpropylthio) ethyl, (1,1-dimethylethylthio)ethyl, n-pentylthioethyl, (1-methylbutylthio)ethyl, (2-methylbutylthio)ethyl, (3-methylbutylthio)ethyl, (2,2-dimethylpropylthio)ethyl, (1-ethylpropylthio) ethyl, n-hexylthioethyl, (1,1-dimethylpropylthio) ethyl,(1,2-dimethylpropylthio)ethyl, (1-methylpentylthio)ethyl, (2-methylpentylthio) ethyl, (3-methylpentylthio)ethyl, (4-methylpentylthio)ethyl, (1,1-dimethylbutylthio) ethyl, (1,2-dimethylbutylthio)ethyl, (1,3-dimethylbutylthio)ethyl, (2,2-dimethylbutylthio) ethyl, (2,3-dimethylbutylthio)ethyl, (3,3-dimethylbutylthio)ethyl, (1-ethylbutylthio)ethyl, (2-ethylbutylthio)ethyl, (1,1,2-trimethylpropylthio) ethyl, (1,2,2-trimethylpropylthio)ethyl, (1-ethyl-1-methylpropylthio)ethyl, (1-ethyl-2-methylpropylthio)ethyl, 2-(methylthio)propyl, 3-(methylthio)propyl or 2-(ethylthio)propyl;

($C_l$–$C_6$-alkoxy)carbonyl-$C_l$–$C_6$-alkyl, eg. methoxycarbonylmethyl, ethoxycarbonylmethyl, n-propoxycarbonylmethyl, (1-methylethoxycarbonyl)methyl, n-butoxycarbonylmethyl, (1-methylpropoxycarbonyl)methyl, (2-methylpropoxycarbonyl)methyl, (1,1-dimethylethoxycarbonyl)methyl, n-pentyloxycarbonylmethyl, (1-methylbutoxycarbonyl)methyl, (2-methylbutoxycarbonyl)methyl, (3-methylbutoxycarbonyl)methyl, (1,1-dimethylpropoxycarbonyl)methyl, (1,2-dimethylpropoxycarbonyl)methyl, (2,2-dimethylpropoxycarbonyl)methyl, (1-ethylpropoxycarbonyl)methyl, n-hexyloxycarbonylmethyl, (1-methylpentyloxycarbonyl)methyl, (2-methylpentyloxycarbonyl)methyl, (3-methylpentyloxycarbonyl)methyl, (4-methylpentyloxycarbonyl)methyl, (1,1-dimethylbutoxycarbonyl)methyl, (1,2-dimethylbutoxycarbonyl)methyl, (1,3-dimethylbutoxycarbonyl)methyl, (2,2-dimethylbutoxycarbonyl)methyl, (2,3-dimethylbutoxycarbonyl)methyl, (3,3-dimethylbutoxycarbonyl)methyl, (1-ethylbutoxycarbonyl)methyl, (2-ethylbutoxycarbonyl)methyl, (1,1,2-trimethylpropoxycarbonyl)methyl, (1,2,2-trimethylpropoxycarbonyl)methyl, (1-ethyl-1-methylpropoxycarbonyl)methyl, (1-ethyl-2-methylpropylcarbonyl)methyl, methoxycarbonylethyl, ethoxycarbonylethyl, n-propoxycarbonylethyl, (1-methylethoxycarbonyl) ethyl, n-butoxycarbonylethyl, (1-methylpropoxycarbonyl)ethyl, (2-methylpropoxycarbonyl)ethyl, (1,1-dimethylethoxycarbonyl)ethyl, n-pentyloxycarbonylethyl, (1-methylbutoxycarbonyl)ethyl, (2-methylbutoxycarbonyl)ethyl, (3-methylbutoxycarbonyl)ethyl, (1,1-dimethylpropoxycarbonyl)ethyl, (1,2-dimethylpropoxycarbonyl)ethyl, (2,2-dimethylpropoxycarbonyl)ethyl, (1-ethylpropoxycarbonyl)ethyl, n-hexyloxycarbonylethyl, (1-methylpentyloxycarbonyl)ethyl, (2-methylpentyloxycarbonyl)ethyl, (3-methylpentyloxycarbonyl)ethyl, (4-methylpentyloxycarbonyl)ethyl, (1,1-dimethylbutoxycarbonyl)ethyl, (1,2-dimethylbutoxycarbonyl)ethyl, (1,3-dimethylbutoxycarbonyl)ethyl, (2,2-dimethylbutoxycarbonyl)ethyl, (2,3-dimethylbutoxycarbonyl)ethyl, (3,3-dimethylbutoxycarbonyl)ethyl, (1-ethylbutoxycarbonyl)ethyl, (2-ethylbutoxycarbonyl)ethyl, (1,1,2-trimethylpropoxycarbonyl)ethyl, (1,2,2-trimethylpropoxycarbonyl)ethyl, (1-ethyl-1-methylpropoxycarbonyl)ethyl, (1-ethyl-2-methylpropylcarbonyl)ethyl, 3-(methoxycarbonyl)propyl, 2-(methoxycarbonyl)propyl or 2-ethoxycarbonyl)propyl;

($C_1$–$C_6$-alkylamino)carbonyl-$C_1$–$C_6$-alkyl, eg. methylaminocarbonylmethyl, ethylaminocarbonylmethyl, n-propylaminocarbonylmethyl, (1-methylethylaminocarbonyl)methyl, n-butylaminocarbonylmethyl, (1-methylpropylaminocarbonyl)methyl, (2-methylpropylaminocarbonyl)methyl,(1,1-dimethylethylaminocarbonyl)methyl, n-pentylaminocarbonylmethyl, (1-methylbutylaminocarbonyl)methyl, (2-methylbutylaminocarbonyl)methyl, (3-methylbutylaminocarbonyl)methyl, (1,1-dimethylpropylaminocarbonyl)methyl, (1,2-dimethylpropylaminocarbonyl)methyl, (2,2-dimethylpropylaminocarbonyl)methyl, (1-ethylpropylaminocarbonyl)methyl, (n-hexylaminocarbonyl)methyl, (1-methylpentylaminocarbonyl)methyl, (2-methylpentylaminocarbonyl)methyl, (3-methylpentylaminocarbonyl)methyl,(1,2-dimethylbutylaminocarbonyl)methyl, (1,3-dimethylbutylaminocarbonyl)methyl, (2,2-dimethylbutylaminocarbonyl)methyl, (2,3-dimethylbutylaminocarbonyl)methyl, (3,3-dimethylbutylaminocarbonyl)methyl, (1-ethylbutylaminocarbonyl)methyl, (2-ethylbutylaminocarbonyl)methyl, (1,1,2-trimethylpropylaminocarbonyl)methyl, (1,2,2-trimethylpropylaminocarbonyl)methyl, (1-ethyl-1-methylpropylcarbonyl)methyl, (1-ethyl-2-methylpropylaminocarbonyl)methyl, methylaminocarbonylethyl, ethylaminocarbonylethyl, n-propylaminocarbonylethyl, (1-methylethylaminocarbonyl)ethyl, n-butylaminocarbonylethyl, (1-methylpropylaminocarbonyl)ethyl, (2-methylpropylaminocarbonyl)ethyl, (1,1-dimethylethylaminocarbonyl)ethyl, n-pentylaminocarbonylethyl, (1-methylbutylaminocarbonyl)ethyl, (2-methylbutylaminocarbonyl)ethyl, (3-methylbutylaminocarbonyl)ethyl, (1,1-dimethylpropylaminocarbonyl)ethyl, (1,2-dimethylpropylaminocarbonyl)ethyl, (2,2-dimethylpropylaminocarbonyl)ethyl, (1-ethylpropylaminocarbonyl)ethyl, (n-hexylaminocarbonyl)ethyl, (1-methylpentylaminocarbonyl)ethyl, (2-methylpentylaminocarbonyl)ethyl, (3-methylpentylaminocarbonyl)ethyl, (1,2-dimethylbutylaminocarbonyl)ethyl, (1,3-dimethylbutylaminocarbonyl)ethyl, (2,2-dimethylbutylaminocarbonylethyl, (2,3-dimethylbutylaminocarbonyl)ethyl, (3,3-dimethylethylbutylaminocarbonyl)ethyl, (1-ethylbutylaminocarbonyl)ethyl, (2-ethylbutylaminocarbonyl)ethyl, (1,1,2-trimethylpropylaminocarbonyl)ethyl, (1,2,2-trimethylpropylaminocarbonyl)ethyl, (1-ethyl-1-methylpropylcarbonyl)ethyl, (1-ethyl-2-methylpropylaminocarbonyl)ethyl, 3-(methylaminocarbonyl)propyl or 2-(methylaminocarbonyl)propyl;

di-($C_1$–$C_6$-alkyl)aminocarbonyl-($C_1$–$C_6$-alkyl), eg. N,N-dimethylaminocarbonylmethyl, N,N-diethylaminocarbonylmethyl, N,N-diisopropylaminocarbonylmethyl, N,N-dibutylaminocarbonylmethyl, N,N-di-(1-methylpropyl)aminocarbonylmethyl, N,N-di-(2-methylpropyl)aminocarbonylmethyl, N,N-di-(1,1-dimethylethyl)aminocarbonylmethyl, N-ethyl-N-methylaminocarbonylmethyl, N-methyl-N-propylaminocarbonylmethyl, N-methyl-N-(1-methylethyl)aminocarbonylmethyl, N-butyl-N-methylaminocarbonylmethyl, N-methyl-N-(1-methylpropyl)aminocarbonylmethyl, N-methyl-N-(2-methylpropyl)aminocarbonylmethyl, N-(1,1-dimethylethyl)-N-methylaminocarbonylmethyl, N-ethyl-N-propylaminocarbonylmethyl, N-ethyl-N-(1-methylethyl)aminocarbonylmethyl, N-butyl-N-ethylaminocarbonylmethyl, N-ethyl-N-(1-methylpropyl)aminocarbonylmethyl, N-ethyl-N-(2-methylpropyl)aminocarbonylmethyl, N-ethyl-N-(1,1-dimethylethyl)aminocarbonylmethyl, N-(1-methylethyl)-N-propylaminocarbonylmethyl, N-butyl-N-propylaminocarbonylmethyl, N-(1-methylpropyl)-N-propylaminocarbonylmethyl, N-(2-methylpropyl)-N-propylaminocarbonylmethyl, N-(1,1-dimethylethyl)-N-propylaminocarbonylmethyl, N-butyl-N-(1-methylethyl)aminocarbonylmethyl, N-(1-methylethyl)-N-(1-methylpropyl)aminocarbonylmethyl, N-(1-methylethyl)-N-(2-methylpropyl)aminocarbonylmethyl, N-(1,1-dimethylethyl)-N-(1-methylethyl)aminocarbonylmethyl, N-butyl-N-(1-methylpropyl)aminocarbonylmethyl, N-butyl-N-(2-methylpropyl)aminocarbonylmethyl, N-butyl-N-(1,1-dimethylethyl)aminocarbonylmethyl, N-(1-methylpropyl)-N-(2-methylpropyl)aminocarbonylmethyl, N-(1,1-dimethylethyl)-N-(1-methylpropyl)aminocarbonylmethyl, N-(1,1-dimethylethyl)-N-(2-methylpropyl)aminocarbonylmethyl, N,N-dimethylaminocarbonylethyl, N,N-diethylaminocarbonylethyl, N,N-diisopropylaminocarbonylethyl, N,N- dibutylaminocarbonylethyl, N,N-dibutylaminocarbonylethyl, N,N-di-(1-methylpropyl)aminocarbonylethyl, N,N-di-(2-methylpropyl)aminocarbonylethyl, N,N-di-(1,1-dimethylethyl)aminocarbonylethyl, N-ethyl-N-methylaminocarbonylethyl, N-methyl-N-propylaminocarbonylethyl, N-methyl-N-(1-methylethyl)aminocarbonylethyl, N-butyl-N-methylaminocarbonylethyl, N-methyl-N-(1-methylpropyl)aminocarbonylethyl, N-methyl-N-(2-methylpropyl)aminocarbonylethyl, N-(1,1-dimethylethyl)-N-methylaminocarbonylethyl, N-ethyl-N-propylaminocarbonylethyl, N-ethyl-N-(1-methylethyl)aminocarbonylethyl, N-butyl-N-ethylaminocarbonylethyl, N-ethyl-N-(1-methylpropyl)aminocarbonylethyl, N-ethyl-N-(2-methylpropyl)aminocarbonylethyl, N-ethyl-N-(1,1-dimethylethyl)aminocarbonylethyl, N-(1-methylethyl)-N-propylaminocarbonylethyl, N-butyl-N-propylaminocarbonylethyl, N-(1-methylpropyl)-N-propylaminocarbonylethyl, N-(2-methylpropyl)-N-propylaminocarbonylethyl, N-(1,1-dimethylethyl)-N-propylaminocarbonylethyl, N-butyl-N-(1-methylethyl)aminocarbonylethyl, N-(1-methylethyl)-N-(1-methylpropyl)aminocarbonylethyl, N-(1-methylethyl)-N-(2-methylpropyl)aminocarbonylethyl, N-(1,1-dimethylethyl)-N-(1-methylethyl)aminocarbonylethyl, N-butyl-N-(1-methylpropyl)aminocarbonylethyl, N-butyl-N-(2-methylpropyl)aminocarbonylethyl, N-butyl-N-(1,1-dimethylethyl)aminocarbonylethyl, N-(1-methylpropyl)-N-(2-methylpropyl)aminocarbonylethyl, N-(1,1-dimethylethyl)-N-(2-methylpropyl)aminocarbonylethyl, N-(1,1-dimethylethyl)-N-(2-methylpropyl)aminocarbonylethyl, 3-N,N-(dimethylaminocarbonyl)propyl, 3-N,N-(diethylaminocarbonyl)propyl, 2-N,N-dimethylaminocarbonylpropyl or 1-N,N-dimethylaminocarbonylpropyl;

$C_1$–$C_6$-alkyloximino-$C_1$–$C_6$-alkyl, eg. methoximinomethyl, ethoximinomethyl, n-propoximinomethyl, (1-methylethoximino)methyl, n-butoximinoethyl, (1-methylpropoximino)methyl, (2-methylpropoximino)methyl, (1,1-dimethylethoximino)methyl, n-pentoximinomethyl, (1-methylbutoximino)methyl, (2-methylbutoximino)methyl, (3-methylbutoximino)methyl, (2,2-dimethylpropoximino)methyl, (1-ethylpropoximino)methyl, n-hexoximinomethyl, (1,1-dimethylpropoximino)methyl, (1,2-dimethylpropoximino)methyl, (1-methylpentoximino)methyl, (2-methylpentoximino)methyl, (3-methylpentoximino)methyl, (4-methylpentoximino)methyl, (1,1-dimethylbutoximino)methyl, (1,2-dimethylbutoximino)methyl, (1,3-dimethylbutoximino)methyl, (2,2-dimethylbutoximino)methyl, (2,3-dimethylbutomino)methyl, (3,3-dimethylbutoximino)methyl, (1-ethylbutoximino)methyl, (2-ethylbutoximino)methyl, (1,1,2-trimethylpropoximino)-methyl, (1,2,2-trimethylpropoximino)methyl, (1-ethyl-1-methylpropoximino)methyl, (1-ethyl-2-methylpropoximino)methyl, methoximinoethyl, ethoximinoethyl, N-propoximinoethyl, (1-methylethoximino)ethyl, n-butoximinoethyl, (1-methylpropoximino)ethyl, (2-methylpropoximino)ethyl, (1,1-dimethylethoximino)ethyl, n-pentoximinoethyl, (1-methylbutoximino)ethyl, (2-methylbutoximino)ethyl, (3-methylbutoximino)ethyl, (2,2-dimethylpropoximino)ethyl, (1-ethylpropoximino)ethyl, n-hexoximino-ethyl, (1,1-dimethylpropoximino)ethyl, (1,2-dimethylpropoximino)ethyl, (1-methylpentoximino)ethyl, (2-methylpentoximino)ethyl, (3-methylpentoximino)ethyl, (4-methylpentoximino)ethyl, (1,1-dimethylbutoximino)ethyl, (1,2-dimethylbutoximino)ethyl, (1,2-dimethylbutoximino)ethyl, (1,3-dimethylbutoximino)ethyl, (2,2-dimethylbutoximino)ethyl, (2,3-dimethylbutoximino)ethyl, (3,3-dimethylbutoximino)ethyl, (1-ethylbutoximino)ethyl, (2-ethylbutoximino)ethyl, (1,1,2-trimethylpropoximino)ethyl, (1,2,2-trimethylpropoximino)ethyl, (1-ethyl-1-methylpropoximino)ethyl, (1-ethyl-2-methylpropoximino)ethyl, 2-(methoximino)propyl, 3-(methoximino)propyl or 2-(ethoximino)propyl;

di-($C_1$–$C_6$-alkoxy)-$C_2$–$C_6$-alkyl, eg. 2,2-dimethoxyethyl, 2,2-diethoxyethyl, 2,2-di-(n-propoxy)ethyl, 2,2-di-(1-methylethoxy)ethyl, 2,2-dibutoxyethyl, 2,2-di-(1-methylpropoxy)ethyl, 2,2-di-(2-methylpropoxy)ethyl, 2,2-di-(1,1-dimethylethoxy)ethyl, 2-(ethoxy)-2-(methoxy)ethyl, 2-(methoxy)-2-(propoxy)ethyl, 2-(methoxy)-2-(1-methylethoxy)ethyl, 2-(butoxy)-2-(methoxy)ethyl, 2-(methoxy)-2-(1-methylpropoxy)ethyl, 2-(methoxy)-2-(2-methylpropoxy)ethyl, 2-(1,1-dimethylethoxy)-2-(methoxy)ethyl, 2-(ethoxy)-2-(propoxy)ethyl, 2-(ethoxy)-2-(1-methylethoxy)ethyl, 2-(butoxy)-2-(ethoxy)-ethyl, 2-(ethoxy)-2-(1-methylpropoxy)ethyl, 2-(ethoxy)-2-(2-methylpropoxy)ethyl, 2-(ethoxy)-2-(1,1-dimethylethoxy)ethyl, 2-(1-methylethoxy)-2-(propoxy)ethyl, 2-(butoxy)-2-(propoxy)ethyl, 2-(1-methylpropoxy)-2-(propoxy)ethyl, 2-(2-methylpropoxy)-2-(propoxy)ethyl, 2-(1,1-dimethylethoxy)-2-(propoxy)ethyl, 2-(butoxy)-2-(1-methylethoxy)ethyl, 2-(1-methylethoxy)-2-(1-methylpropoxy)ethyl, 2-(1-methylethoxy)-2-(2-methylpropoxy)ethyl, 2-(1,1-dimethylethoxy)-2-(1-methylethoxy)ethyl, 2-(butoxy)-2-(1-methylpropoxy)ethyl, 2-(butoxy)-2-(2-methylpropoxy)ethyl, 2-(butoxy)-2-(1,1-dimethylethoxy)ethyl, 2-(1-methylpropoxy)-2-(2-methylpropoxy)ethyl, 2-(1,1-dimethylethoxy)-2-(1-methylpropoxy)ethyl or 2-(1,1-dimethylethoxy)-2-(2-methylpropoxy)ethyl;

di-($C_1$–$C_6$-alkylthio)-$C_2$–$C_6$-alkyl, eg. 2,2-(dimethylthio)ethyl, 2,2-(diethylthio)ethyl, 2,2-di-(n-propylthio)ethyl, 2,2-di-(1-methylethylthio)ethyl, 2,2-(dibutylthio)ethyl, 2,2-di-(1-methylpropylthio)ethyl, 2,2-di-(2-methylpropylthio)ethyl, 2,2-di-(1,1-dimethylethylthio)ethyl, 2-(ethylthio)-2-(methylthio)ethyl, 2-(methylthio)-2-(propylthio)-ethyl, 2-(methylthio)-2-(1-methylethylthio)ethyl, 2-(butylthio)-2-(methylthio)ethyl, 2-(methylthio)-2-(1-methylpropyl thio)ethyl, 2-(methylthio)-2-(2-methylpropylthio)ethyl, 2-(1,1-dimethylethylthio)-

2-(methylthio)ethyl, 2-(ethylthio)-2-(propylthio) ethyl, 2-(ethylthio)-2-(1-methylethylthio)ethyl, 2-(butylthio)-2-(ethylthio)ethyl, 2-(ethylthio)-2-(1-methylpropylthio)ethyl, 2-(ethylthio)-2-(2-methylpropylthio)ethyl, 2-(ethylthio)-2-(1,1-dimethylethylthio)ethyl, 2-(1-methylethylthio)-2-(propylthio)ethyl, 2-(butylthio)-2-(propylthio)ethyl, 2-(1-methylpropylthio)-2-(propylthio)ethyl, 2-(2-methylpropylthio)-2-(propylthioethyl), 2-(1,1-dimethylethylthio)-2-(propylthio)ethyl, 2-(butylthio)-2-(1-methylethylthio)ethyl, 2-(1-methylethylthio)-2-(1-methylpropylthio)ethyl, 2-(1-methylethylthio)-2-(2-methylpropylthio)ethyl, 2-(1,1-dimethylethylthio)-2-(1-methylethylthio)ethyl, 2-(butylthio)-2-(1-methylpropylthio)ethyl, 2-(butylthio)-2-(2-methylpropylthio)ethyl, 2-(butylthio)-2-(1,1-dimethylethylthio)ethyl, 2-(1-methylpropylthio)-2-(2-methylpropylthio)ethyl, 2-(1,1-dimethylethylthio)-2-(1-methylpropylthio) ethyl or 2-(1,1-dimethylethylthio)-2-(2-methylpropylthio)ethyl;

$C_3$–$C_6$-haloalkenyl, eg. 2-chloroprop-2-enyl, 3-chloroprop-2-enyl, 2,3-dichloroprop-2-enyl, 3,3-dichloroprop-2-enyl, 2,3,3-trichloroprop-2-enyl, 2,3-dichlorobut-2-enyl, 2-bromoprop-2-enyl, 3-bromoprop-2-enyl, 2,3-dibromoprop-2-enyl, 3,3-dibromoprop-2-enyl, 2,3,3-tribromoprop-2-enyl or 2,3-dibromobut-2-enyl;

phenyl or benzyl, where the phenyl ring in each case may carry one to three radicals:
cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, such as methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 1,1-dimethylpropylthio, 1,2-dimethylproyplthio, 2,2-dimethylpropylthio, 1-ethylpropylthio, n-hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutlythio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, $C_1$–$C_6$-haloalkylthio, eg. difluoromethylthio, trifluoromethylthio, chlorodifluoromethylthio, bromodifluoromethylthio, 2-fluoroethylthio, 2,2-difluoroethylthio, 2,2,2-trifluoroethylthio, 2-chloroethylthio, 2-bromoethylthio, 2-iodoethylthio, 2,2,2-trichloroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio, 3-fluoropropylthio, 2-fluoropropylthio, 2,2-difluoropropylthio, 2,3-difluoropropylthio, 3-chloropropylthio, 2-chloropropylthio, 2,3-dichloropropylthio, 3-bromopropylthio, 2-bromopropylthio, 3,3,3-trichloropropylthio, 3,3,3-trifluoropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio or 4-bromobutylthio, ($C_1$–$C_6$-alkoxy)carbonyl, eg. methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl, 1,1-dimethylethoxycarbonyl, n-pentyloxycarbonyl, 1-methylbutoxycarbonyl, 2-methylbutoxycarbonyl, 3-methylbutoxycarbonyl, 1,1-dimethylpropoxycarbonyl, 1,2-dimethylpropoxycarbonyl, 2,2-dimethylpropoxycarbonyl, 1-ethylpropoxycarbonyl, hexyloxycarbonyl, 1-methylpentyloxycarbonyl, 2-methylpentyloxycarbonyl, 3-methylpentyloxycarbonyl, 4-methylpentyloxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropylcarbonyl.

In particular, $R^7$ is hydrogen, $C_1$–$C_4$-alkyl, in particular methyl, ethyl, n-propyl, 1-methylethyl, 1-methylpropyl or 2-methylpropyl;

$C_3$- or $C_4$-alkenyl, in particular prop-2-en-2-yl, prop-2-en-1-yl, but-2-en-1-yl, but-2-en-1-yl, 2-methylprop-2-en-1-yl or but-1-en-3-yl;

$C_3$- or $C_4$-alkynyl, in particular prop-2-yn-1-yl, n-but-1-yn-3-yl or n-but-2-yn-1-yl;

$C_3$–$C_6$-cycloalkyl, in particular cyclopropyl, cyclopentyl or cyclohexyl;

$C_1$–$C_4$-haloalkyl, in particular fluoromethyl, difluoromethyl, trifluoromethyl, 2-fluoroethyl, 2,2-difluoroethyl, 2,2,2-tri- fluoroethyl, 2-chloroethyl or 2,2,2-trichloroethyl;

$C_1$–$C_4$-cyanoalkyl, in particular cyanomethyl or 1-cyanoeth-1-yl;

$C_1$–$C_4$-alkoxy-$C_1$–$C_4$-alkyl, in particular methoxymethyl or methoxyethyl;

$C_1$–$C_4$-alkylthio-$C_1$–$C_4$-alkyl, in particular methylthiomethyl or methylthioethyl;

$C_1$–$C_4$-alkoxycarbonyl-$C_1$–$C_4$-alkyl, in particular methoxycarbonylmethyl, ethoxycarbonylmethyl, 1-methylethoxycarbonylmethyl, 2-methylpropoxycarbonylmethyl, 1-(methoxycarbonyl)eth-1-yl, 1-(ethoxycarbonyl)eth-1-yl, 1-(1-methylethoxycarbonyl)eth-1-yl, 1-(methoxycarbonyl)prop-1-yl, 1-(ethoxycarbonyl)prop-1-yl, 1-(methoxycarbonyl)but-1-yl or 1-(ethoxycarbonyl)but-1-yl;

($C_1$–$C_4$-alkylamino)carbonyl-($C_1$–$C_4$)-alkyl, in particular methylaminocarbonylmethyl, ethylaminocarbonylmethyl, 1-methylethylaminocarbonylmethyl, 2-methylpropylaminocarbonylmethyl, 1-(methylaminocarbonyl)eth-1-yl, 1-(ethylaminocarbonyl)eth-1-yl, 1-(1-methylethylaminocarbonyl)eth-1-yl, 1-(methylaminocarbonyl)prop-1-yl, 1-(ethylaminocarbonyl)prop-1-yl, 1-(methylaminocarbonyl)but-1-yl or 1-(ethylaminocarbonyl)but-1-yl;

di-($C_1$–$C_4$-alkyl)aminocarbonyl-($C_1$–$C_4$-alkyl), in particular N,N-dimethylaminocarbonylmethyl, N,N-diethylaminocarbonylmethyl, N-methyl-N-ethylaminocarbonylmethyl, N-isopropyl-N-methylaminocarbonylmethyl, 1-(N,N-dimethylaminocarbonyl)-1-ethyl, 1-(N,N-diethylaminocarbonyl)eth-1-yl, 1-(N-methyl-N-ethylaminocarbonyl)eth-1-yl, 1-(N,N-dimethylaminocarbonyl)-1-propyl or 1-(N,N-diethylaminocarbonyl)prop-1-yl;

alkyloximinoalkyl of in total not more than 6 carbon atoms, in particular methoximinomethyl, ethoximinomethyl, methoximinoethyl or ethoximinoethyl;

dialkoxyalkyl of in total not more than 8 carbon atoms, in particular 2,2-dimethoxyethyl or 2,2-diethoxyethyl;

dialkylthioalkyl of in total not more than 8 carbon atoms, in particular 2,2-(dimethylthio)ethyl or 2,2-(diethylthio)ethyl;

$C_3$- or $C_4$-haloalkenyl, in particular 2-chloro-2-propenyl;

unsubstituted or monosubstituted phenyl or benzyl, in particular phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2-methoxycarbonylphenyl, 3-methoxycarbonylphenyl, 4-methoxycarbonylphenyl or benzyl;

$R^8$, $R^9$ and $R^{10}$, independently of one another, are each
($C_1$–$C_6$-alkyl)carbonyl as stated above,
($C_1$–$C_6$-haloalkyl)carbonyl as stated above or
one of the radicals stated for $R^7$.

The following are preferred:
($C_1$–$C_4$-alkyl)carbonyl, in particular methylcarbonyl, ethylcarbonyl or propylcarbonyl,
($C_1$–$C_4$-haloalkyl)carbonyl, in particular chloroacetyl, trichloroacetyl, fluoroacetyl or trifluoroacetyl;
hydrogen;
$C_1$–$C_4$-alkyl, in particular methyl, ethyl, n-propyl, 1-methylethyl, 1-methylpropyl or 2-methylpropyl;
$C_3$- or $C_4$-alkenyl, in particular prop-2-en-2-yl, prop-2-en-1-yl, but-2-en-2-yl, but-2-en-1-yl, 2-methylprop-2-en-1-yl or but-1-en-3-yl;
$C_3$- or $C_4$-Alkynyl, in particular prop-2-yn-1-yl, n-but-1-yn-3-yl or n-but-2-yn-1-yl;
$C_3$–$C_6$-cycloalkyl, in particular cyclopropyl, cyclopentyl or cyclohexyl;
$C_1$–$C_4$-haloalkyl, in particular fluoromethyl, difluoromethyl, trifluoromethyl, 2-fluoroethyl, 2,2-difluoroethyl, 2,2,2-trifluoroethyl, 2-chloroethyl or 2,2,2-trichloroethyl;
$C_1$–$C_4$-cyanoalkyl, in particular cyanomethyl or 1-cyanoeth-1-yl;
$C_1$–$C_4$-alkoxy-$C_1$–$C_4$-alkyl, in particular methoxymethyl or methoxyethyl;

$C_1$–$C_4$-alkylthio-$C_1$–$C_4$-alkyl, in particular methylthiomethyl or methylthioethyl;

$C_1$–$C_4$-alkoxycarbonyl-$C_1$–$C_4$-alkyl, in particular one of the radicals mentioned individually here for $R^7$;

($C_1$–$C_4$-alkylamino)carbonyl-($C_1$–$C_4$)-alkyl, in particular one of the radicals mentioned individually here for $R^7$;

di-($C_1$–$C_4$-alkyl)aminocarbonyl-($C_1$–$C_4$-alkyl), in particular one of the radicals mentioned individually here for $R^7$;

alkyloximinoalkyl of in total not more than 6 carbon atoms, in particular one of the radicals mentioned individually here for $R^7$;

dialkoxyalkyl of in total not more than 8 carbon atoms, in particular 2,2-dimethoxyethyl or 2,2-diethoxyethyl;

dialkylthioalkyl of in total not more than 8 carbon atoms, in particular 2,2-(dimethylthio)ethyl or 2,2-(diethylthio)ethyl;

$C_3$- or $C_4$-haloalkenyl, in particular 2-chloro-2-propenyl;

unsubstituted or monosubstituted phenyl or benzyl, in particular as mentioned individually here for $R^7$;

$R^8$ and $R^9$ together may furthermore form a 4-membered to 6-membered alkylene chain in which one methylene unit may be replaced by oxygen or by a $C_1$–$C_4$-alkylimino group, and, together with the nitrogen to which the two substituents are bonded, may thus form a 5-membered to 7-membered heterocyclic structure, for example 1-pyrrolidinyl, 1-piperidinyl, 1-hexahydroazepinyl, 4-morpholinyl or 4-methylhexahydropyrazin-1-yl.

With regard to the use of the novel substituted triazolinones of the formula I as compounds having a herbicidal and/or defoliant/desiccant action, the variables preferably having the following meanings:

$R^1$ is a radical selected from the group consisting of H, $CH_3$, $CH_2F$, $CHF_2$, $CF_3$, $CH_2CH_2F$, $CH_2CF_3$ and $CF_2CF_3$;

$R^2$ is a radical selected from the group consisting of H, $CH_3$, $C_2H_5$, n-$C_3H_7$, i-$C_3H_7$, n-$C_4H_9$, i-$C_4H_9$, s-$C_4H_9$, t-$C_4H_9$, $CH_2F$, $CHF_2$ and $CF_3$;

$R^3$ is a radical selected from the group consisting of H, F, Cl, Br and I;

$R^4$ is a radical selected from the group consisting of F, Cl, Br, CN, $CH_3$, $CF_3$, $OCH_3$ and $OCF_3$;

$R^5$ is a radical selected from the group consisting of Cl, Br, I, F, $NO_2$ and CN;

$R^6$ is a radical selected from the group 6.01–6.310 (Table 1), where $R^1$, $R^2$, $R^3$, $R^4$, $R^5$ and $R^6$ may be combined as desired with one another.

TABLE 1

| No. | $R^6$ |
|---|---|
| 6.01 | OH |
| 6.02 | $OCH_3$ |
| 6.03 | $OC_2H_5$ |
| 6.04 | O-n-$C_3H_7$ |
| 6.05 | O—CH($CH_3$)$_2$ |
| 6.06 | O-n-$C_4H_9$ |
| 6.07 | O-i-$C_4H_9$ |
| 6.08 | O-s-$C_4H_9$ |
| 6.09 | O—C($CH_3$)$_3$ |
| 6.10 | O-n-$C_5H_{11}$ |
| 6.11 | O-n-$C_6H_{13}$ |
| 6.12 | O—CH=CH—$CH_3$ |
| 6.13 | O—$CH_2$—CH=$CH_2$ |

TABLE 1-continued

| No. | R⁶ |
|---|---|
| 6.14 | O—C(CH₃)=CH₂ |
| 6.15 | O—C(CH₃)=CH—CH₃ |
| 6.16 | O—CH₂—CH=CH—CH₃ |
| 6.17 | O—CH(CH₃)—CH=CH₂ |
| 6.18 | O—CH₂—C(CH₃)=CH₂ |
| 6.19 | O—CH₂—C≡CH |
| 6.20 | O—CH(CH₃)—C≡CH |
| 6.21 | O—CH₂—C≡C—CH₃ |
| 6.22 | O-cyclopropyl |
| 6.23 | O-cyclopentyl |
| 6.24 | O-cyclohexyl |
| 6.25 | OCH₂F |
| 6.26 | OCHF₂ |
| 6.27 | OCF₃ |
| 6.28 | OCH₂—CH₂F |
| 6.29 | OCH₂—CF₂H |
| 6.30 | OCH₂—CF₃ |
| 6.31 | OCH₂—CH₂Cl |
| 6.32 | OCH₂—CCl₃ |
| 6.33 | OCH₂—CN |
| 6.34 | OCH(CH3)—CN |
| 6.35 | OCH₂—OCH₃ |
| 6.36 | OCH₂—OC₂H₅ |
| 6.37 | OCH₂CH₂—OCH₃ |
| 6.38 | OCH₂CH₂—OC₂H₅ |
| 6.39 | OCH(CH₃)—OCH₃ |
| 6.40 | OCH(CH₃)—OC₂H₅ |
| 6.41 | OCH₂—SCH₃ |
| 6.42 | OCH₂CH₂—SCH₃ |
| 6.43 | OCH₂CO—OCH₃ |
| 6.44 | OCH₂CO—OC₂H₅ |
| 6.45 | OCH₂CO—OCH(CH₃)₂ |
| 6.46 | OCH(CH₃)CO—OCH₃ |
| 6.47 | OCH(CH₃)CO—OC₂H₅ |
| 6.48 | OCH(C₂H₅)CO—OCH₃ |
| 6.49 | OCH(C₂C₅)CO—OC₂H₅ |
| 6.50 | OCH₂CO—NH—CH₃ |
| 6.51 | OCH₂CO—NH—C₂H₅ |
| 6.52 | OCH(CH₃)CO—NH—CH₃ |
| 6.53 | OCH(CH₃)CO—NH—C₂H₅ |
| 6.54 | OCH(C₂H₅)CO—NH—CH₃ |
| 6.55 | OCH(C₂H₅)CO—NH—C₂H₅ |
| 6.56 | OCH₂CO—N(CH₃)₂ |
| 6.57 | OCH₂CO—N(C₂H₅)₂ |
| 6.58 | OCH₂CO—N(CH₃)—C₂H₅ |
| 6.59 | OCH(CH₃)CO—N(CH₃)₂ |
| 6.60 | OCH(C₂H₅)CO—N(CH₃)₂ |
| 6.61 | OCH₂CH=N—OCH₃ |
| 6.62 | OCH₂CH=N—OC₂H₅ |
| 6.63 | OCH₂CH(OCH₃)₂ |
| 6.64 | OCH₂CH(OC₂H₅)₂ |
| 6.65 | OCH₂CH(SCH₃)₂ |
| 6.66 | OCH₂CH(SC₂H₅)₂ |
| 6.67 | OCH₂C(Cl)=CH₂ |
| 6.68 | OCH₂C(Cl)=CCl₂ |
| 6.69 | O-phenyl |
| 6.70 | O-(2-F-phenyl) |
| 6.71 | O-(3-F-phenyl) |
| 6.72 | O-(4-F-phenyl) |
| 6.73 | O-(2-Cl-phenyl) |
| 6.74 | O-(3-Cl-phenyl) |
| 6.75 | O-(4-Cl-phenyl) |
| 6.76 | O-(2-CH₃-phenyl) |
| 6.77 | O-(3-CH₃-phenyl) |
| 6.78 | O-(4-CH₃-phenyl) |
| 6.79 | O-(2-CF₃-phenyl) |
| 6.80 | O-(3-CF₃-phenyl) |
| 6.81 | O-(4-CF₃-phenyl) |
| 6.82 | O-(2-CH₃O-phenyl) |
| 6.83 | O-(3-CH₃O-phenyl) |
| 6.84 | O-(4-CH₃O-phenyl) |
| 6.85 | O-(2-CO₂CH₃-phenyl) |
| 6.86 | O-(3-CO₂CH₃-phenyl) |
| 6.87 | O-(4-CO₂CH₃-phenyl) |
| 6.88 | O—CH₂-phenyl |
| 6.89 | SH |
| 6.90 | SCH₃ |
| 6.91 | SC₂H₅ |
| 6.92 | S-n-C₃H₇ |
| 6.93 | S—CH(CH₃)₂ |
| 6.94 | S-n-C₄H₉ |
| 6.95 | S-i-C₄H₉ |
| 6.96 | S-s-C₄H₉ |
| 6.97 | S—C(CH₃)₃ |
| 6.98 | S-n-C₅H₁₁ |
| 6.99 | S-n-C₆H₁₃ |
| 6.100 | S—CH=CH—CH₃ |
| 6.101 | S—CH₂CH=CH₂ |
| 6.102 | S—C(CH₃)=CH₂ |
| 6.103 | S—C(CH₃)=CH—CH₃ |
| 6.104 | S—CH₂—CH=CH—CH₃ |
| 6.105 | S—CH(CH₃)—CH=CH₂ |
| 6.106 | S—CH₂—C(CH₃)=CH₂ |
| 6.107 | S—CH₂—C≡CH |
| 6.108 | S—CH(CH₃)C≡CH |
| 6.109 | S—CH₂—C≡C—CH₃ |
| 6.110 | S-cyclopropyl |
| 6.111 | S-cyclopentyl |
| 6.112 | S-cyclohexyl |
| 6.113 | S-CH₂F |
| 6.114 | S-CHF₂ |
| 6.115 | S-CF₃ |
| 6.116 | S—CH₂—CH₂F |
| 6.117 | S—CH₂—CF₂H |
| 6.118 | S—CH₂—CF₃ |
| 6.119 | S—CH₂—CH₂Cl |
| 6.120 | S—CH₂—CCl₃ |
| 6.121 | S—CH₂—CN |
| 6.122 | S—CH(CH₃)—CN |
| 6.123 | S—CH₂—OCH₃ |
| 6.124 | S—CH₂OC₂H₅ |
| 6.125 | S—CH₂CH₂—OCH₃ |
| 6.126 | S—CH₂CH₂—OC₂H₅ |
| 6.127 | S—CH(CH₃)—OCH₃ |
| 6.128 | S—CH(CH₃)—OC₂H₅ |
| 6.129 | SCH₂—SCH₃ |
| 6.130 | SCH₂CH₂—SCH₃ |
| 6.131 | SCH₂CO—OCH₃ |
| 6.132 | SCH₂CO—OC₂H₅ |
| 6.133 | SCH₂CO—OCH(CH₃)₂ |
| 6.134 | SCH(CH₃)CO—OCH₃ |
| 6.135 | SCH(CH₃)CO—OC₂H₅ |
| 6.136 | SCH(C₂H₅)CO—OCH₃ |
| 6.137 | SCH(C₂H₅)CO—OC₂H₅ |
| 6.138 | SCH₂CO—NH—CH₃ |
| 6.139 | SCH₂CO—NH—C₂H₅ |
| 6.140 | SCH(CH₃)CO—NH—CH₃ |
| 6.141 | SCH(CH₃)CO—NH—C₂H₅ |
| 6.142 | SCH(C₂H₅)CO—NH—CH₃ |
| 6.143 | SCH(C₂H₅)CO—NH—C₂H₅ |
| 6.144 | SCH₂CO—N(CH₃)₂ |
| 6.145 | SCH₂CO—N(C₂H₅)₂ |
| 6.146 | SCH(CH₃)CO—N(CH₃)₂ |
| 6.147 | SCH(C₂H₅)CO—N(CH₃)₂ |
| 6.148 | S—CH₂CH=N—OCH₃ |
| 6.149 | S—CH₂CH=N—OC₂H₅ |
| 6.150 | S—CH₂CH(OCH₃)₂ |
| 6.151 | S—CH₂CH(OC₂H₅)₂ |
| 6.152 | S—CH₂CH(SCH₃)₂ |
| 6.153 | S—CH₂CH(SC₂H₅)₂ |
| 6.154 | S—CH₂C(Cl)=CH₂ |
| 6.155 | S—CH₂C(Cl)=CCl₂ |
| 6.156 | S-phenyl |
| 6.157 | S-(2-F-phenyl) |
| 6.158 | S-(3-F-phenyl) |
| 6.159 | S-(4-F-phenyl) |
| 6.160 | S-(2-Cl-phenyl) |
| 6.161 | S-(3-Cl-phenyl) |
| 6.162 | S-(4-Cl-phenyl) |
| 6.163 | S-(2-CH₃-phenyl) |
| 6.164 | S-(3-CH₃-phenyl) |
| 6.165 | S-(4-CH₃-phenyl) |
| 6.166 | S-(2-CF₃-phenyl) |
| 6.167 | S-(3-CF₃-phenyl) |

TABLE 1-continued

| No. | R⁶ |
|---|---|
| 6.168 | S-(4-CF$_3$-phenyl) |
| 6.169 | S-(2-CH$_3$O-phenyl) |
| 6.170 | S-(3-CH$_3$O-phenyl) |
| 6.171 | S-(4-CH$_3$O-phenyl) |
| 6.172 | S-(2-CO$_2$CH$_3$-phenyl) |
| 6.173 | S-(3-CO$_2$CH$_3$-phenyl) |
| 6.174 | S-(4-CO$_2$—CH$_3$-phenyl) |
| 6.175 | S—CH$_2$-phenyl |
| 6.176 | NH$_2$ |
| 6.177 | NH—CH$_3$ |
| 6.178 | NH—C$_2$H$_5$ |
| 6.179 | NH-n-C$_3$H$_7$ |
| 6.180 | NH—CH(CH$_3$)$_2$ |
| 6.181 | NH-n-C$_4$H$_9$ |
| 6.182 | NH-i-C$_4$H$_9$ |
| 6.183 | NH—S—C$_4$H$_9$ |
| 6.184 | NH—C(CH$_3$)$_3$ |
| 6.185 | NH-n-C$_5$H$_{11}$ |
| 6.186 | NH-n-C$_6$H$_{13}$ |
| 6.187 | NH—CH$_2$—CH=CH$_2$ |
| 6.188 | NH—CH(CH$_3$)—CH=CH$_2$ |
| 6.189 | NH—CH$_2$—CH=CH—CH$_3$ |
| 6.190 | NH—CH$_2$—C≡CH |
| 6.191 | NH—CH(CH$_3$)—C≡CH |
| 6.192 | NH-cyclopropyl |
| 6.193 | NH-cyclopentyl |
| 6.194 | NH-cyclohexyl |
| 6.195 | NH-CH$_2$CH$_2$F |
| 6.196 | NH—CH$_2$CHF$_2$ |
| 6.197 | NH—CH$_2$CF$_3$ |
| 6.198 | NH—CH$_2$CH$_2$Cl |
| 6.199 | NH—CH$_2$CCl$_3$ |
| 6.200 | NH—CH$_2$CN |
| 6.201 | NH—CH(CH$_3$)CN |
| 6.202 | NH—CH$_2$CH$_2$—OCH$_3$ |
| 6.203 | NH—CH$_2$CH$_2$—OC$_2$H$_5$ |
| 6.204 | NH—CH$_2$CH$_2$—SCH$_3$ |
| 6.205 | NH—CH$_2$CO—OCH$_3$ |
| 6.206 | NH—CH$_2$CO—OC$_2$H$_5$ |
| 6.207 | NH—CH$_2$CO—OCH(CH$_3$)$_2$ |
| 6.208 | NH—CH(CH$_3$)CO—OCH$_3$ |
| 6.209 | NH—CH(CH$_3$)CO—OC$_2$H$_5$ |
| 6.210 | NH—CH(C$_2$H$_5$)CO—OCH$_3$ |
| 6.211 | NH—CH(C$_2$H$_5$)CO—OC$_2$H$_5$ |
| 6.212 | NH—CH$_2$CO—NH—CH$_3$ |
| 6.213 | NH—CH$_2$CO—NH—C$_2$H$_5$ |
| 6.214 | NH—CH(CH$_3$)CO—NH—CH$_3$ |
| 6.215 | NH—CH(CH$_3$)CO—NH—C$_2$H$_5$ |
| 6.216 | NH—CH(C$_2$H$_5$)CO—NH—CH$_3$ |
| 6.217 | NH—CH$_2$CO—N(CH$_3$)$_2$ |
| 6.218 | NH—CH$_2$CO—N(C$_2$H$_5$)$_2$ |
| 6.219 | NH—CH(CH$_3$)CO—N(CH$_3$)$_2$ |
| 6.220 | NH—CH(CH$_3$)CO—N(C$_2$H$_5$)$_2$ |
| 6.221 | NH—CH$_2$CH=N—OCH$_3$ |
| 6.222 | NH—CH$_2$CH=N—OC$_2$H$_5$ |
| 6.223 | NH—CH$_2$CH(OCH$_3$)$_2$ |
| 6.224 | NH—CH$_2$CH(SCH$_3$)$_2$ |
| 6.225 | NH—CH$_2$CH(SC$_2$H$_5$)$_2$ |
| 6.226 | NH—CH$_2$C(Cl)=CH$_2$ |
| 6.227 | NH—CH$_2$C(Cl)=CCl$_2$ |
| 6.228 | NH-phenyl |
| 6.229 | NH-(2-F-phenyl) |
| 6.230 | NH-(3-F-phenyl) |
| 6.231 | NH-(4-F-phenyl) |
| 6.232 | NH-(2-Cl-phenyl) |
| 6.233 | NH-(3-Cl-phenyl) |
| 6.234 | NH-(4-Cl-phenyl) |
| 6.235 | NH-(2-CH$_3$-phenyl) |
| 6.236 | NH-(3-CH$_3$-phenyl) |
| 6.237 | NH-(4-CH$_3$-phenyl) |
| 6.238 | NH-(2-CF$_3$-phenyl) |
| 6.239 | NH-(3-CF$_3$-phenyl) |
| 6.240 | NH-(4-CF$_3$-phenyl) |
| 6.241 | NH-(2-CH$_3$O-phenyl) |
| 6.242 | NH-(3-CH$_3$O-phenyl) |
| 6.243 | NH-(4-CH$_3$O-phenyl) |
| 6.244 | NH-(2-CO$_2$CH$_3$-phenyl) |
| 6.245 | NH-(3-CO$_2$CH$_3$-phenyl) |
| 6.246 | NH-(4-CO$_2$CH$_3$-phenyl) |
| 6.247 | NH—CH$_2$-phenyl |
| 6.248 | N(CH$_3$)$_2$ |
| 6.249 | N(CH$_3$)—C$_2$H$_5$ |
| 6.250 | N(CH$_3$)—CH(CH$_3$)$_2$ |
| 6.251 | N(CH$_3$)(i-C$_3$H$_7$) |
| 6.252 | N(CH$_3$)(n-C$_4$H$_9$) |
| 6.253 | N(CH$_3$)(i-C$_4$H$_9$) |
| 6.254 | N(CH$_3$)(6-C$_4$H$_9$) |
| 6.255 | N(CH$_3$)—C(CH$_3$)$_3$ |
| 6.256 | N(CH$_3$)(n-C$_5$H$_{11}$) |
| 6.257 | N(CH$_3$)(n-C$_6$H$_{13}$) |
| 6.258 | N(CH$_3$)—CH$_2$—CH=CH$_2$ |
| 6.259 | N(CH$_3$)—CH(CH$_3$)—CH=CH$_2$ |
| 6.260 | N(CH$_3$)—CH$_2$—CH=CH—CH$_3$ |
| 6.261 | N(CH$_3$)—CH$_2$—C≡CH |
| 6.262 | N(CH$_3$)—CH(CH$_3$)—C≡CH |
| 6.263 | N(CH$_3$)-cyclopropyl |
| 6.264 | N(CH$_3$)-cyclopentyl |
| 6.265 | N(CH$_3$)-cyclohexyl |
| 6.266 | N(CH$_3$)—CH$_2$CH$_2$F |
| 6.267 | N(CH$_3$)—CH$_2$CN |
| 6.268 | N(CH$_3$)—CH$_2$CO—OCH$_3$ |
| 6.269 | N(CH$_3$)—CH$_2$CO—OC$_2$H$_5$ |
| 6.270 | N(CH$_3$)—CH(CH$_3$)CO—OCH$_3$ |
| 6.271 | N(CH$_3$)—CH(CH$_3$)CO—OC$_2$H$_5$ |
| 6.272 | N(CH$_3$)—CH(C$_2$H$_5$)CO—OCH$_3$ |
| 6.273 | N(CH$_3$)—CH$_2$CO—NH—CH$_3$ |
| 6.274 | N(CH$_3$)-phenyl |
| 6.275 | N(CH$_3$)(2-F-phenyl) |
| 6.276 | N(CH$_3$)(3-F-phenyl) |
| 6.277 | N(CH$_3$)(4-F-phenyl) |
| 6.278 | N(CH$_3$)(2-Cl-phenyl) |
| 6.279 | N(CH$_3$)(3-Cl-phenyl) |
| 6.280 | N(CH$_3$)(4-Cl-phenyl) |
| 6.281 | N(CH$_3$)(2-CH$_3$-phenyl) |
| 6.282 | N(CH$_3$)(3-CH$_3$-phenyl) |
| 6.283 | N(CH$_3$)(4-CH$_3$-phenyl) |
| 6.284 | N(CH$_3$)(2-CH$_3$O-phenyl) |
| 6.285 | N(CH$_3$)(3-CH$_3$O-phenyl) |
| 6.286 | N(CH$_3$)(4-CH$_3$O-phenyl) |
| 6.287 | N(CH$_3$)(3-CO$_2$CH$_3$-phenyl) |
| 6.288 | N(CH$_3$)(4-CO$_2$CH$_3$-phenyl) |
| 6.289 | N(CH$_3$)(3-CF$_3$-phenyl) |
| 6.290 | N(CH$_3$)(4-CF$_3$-phenyl) |
| 6.291 | N(CH$_3$)—CH$_2$-phenyl |
| 6.292 | N(C$_2$H$_5$)$_2$ |
| 6.293 | N(C$_2$H$_5$)—CH$_2$CO—OCH$_3$ |
| 6.294 | N(n-C$_3$H$_7$)$_2$ |
| 6.295 | NH—OH |
| 6.296 | N(CH$_3$)—OH |
| 6.297 | NH—OCH$_3$ |
| 6.298 | NH—OC$_2$H$_5$ |
| 6.299 | N(CH$_3$)—OCH$_3$ |
| 6.300 | N(CH$_3$)—OC$_2$H$_5$ |
| 6.301 | NH—COCH$_3$ |
| 6.302 | NH—COC$_2$H$_5$ |
| 6.303 | NH—COCF$_3$ |
| 6.304 | NH—COCH$_2$Cl |
| 6.305 | NH—COCH$_2$F |
| 6.306 | NH—COCH(CH$_3$)$_2$ |
| 6.307 | 1-pyrrolidinyl |
| 6.308 | 1-piperidinyl |
| 6.309 | 1-morpholinyl |
| 6.310 | 4-methylpiperazin-1-yl |

The substituted triazolinones of the formula I may be present in the form of their agriculturally useful salts, the type of salt being, as a rule, unimportant. In general, the salts of bases which do not adversely affect the herbicidal action of I are suitable.

Particularly suitable basic salts are those of the alkali metals, preferably sodium salts and potassium salts, those of the alkaline earth metals, preferably calcium salts and magnesium salts, and those of the transition metals, preferably zinc salts and iron salts, and the ammonium salts, which may carry from one to four $C_1$–$C_4$-alkyl or hydroxy-$C_1$–$C_4$-alkyl substituents and/or one phenyl or benzyl substituent, preferably diiisopropylammonium, tetramethylammonium, tetrabutylammonium, trimethylbenzylammonium and trimethyl-(2-hydroxyethyl)ammonium salts, and the phosphonium salts, sulfonium salts and sulfoxonium salts, preferably tri-($C_1$–$C_4$-alkyl)sulfoxonium salts.

With regard to the use of substituted triazolones I as herbicides, the compounds Ia (=I where $R^1$=CHF$_2$, $R^2$=CH$_3$ and $R^6$=OR$^7$) mentioned in Table 2 are very particularly preferred:

TABLE 2

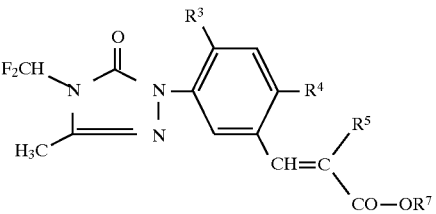

Ia

| No. | $R^3$ | $R^4$ | $R^5$ | $R^7$ |
|---|---|---|---|---|
| Ia.001 | H | Cl | Cl | H |
| Ia.002 | F | Cl | Cl | H |
| Ia.003 | Cl | Cl | Cl | H |
| Ia.004 | H | Cl | Br | H |
| Ia.005 | F | Cl | Br | H |
| Ia.006 | Cl | Cl | Br | H |
| Ia.007 | H | Cl | F | H |
| Ia.008 | F | Cl | F | H |
| Ia.009 | Cl | Cl | F | H |
| Ia.010 | H | Cl | I | H |
| Ia.011 | F | Cl | I | H |
| Ia.012 | Cl | Cl | I | H |
| Ia.013 | H | Cl | NO$_2$ | H |
| Ia.014 | F | Cl | NO$_2$ | H |
| Ia.015 | Cl | Cl | NO$_2$ | H |
| Ia.016 | H | Cl | CN | H |
| Ia.017 | F | Cl | CN | H |
| Ia.018 | Cl | Cl | CN | H |
| Ia.019 | H | Cl | Cl | CH$_3$ |
| Ia.020 | F | Cl | Cl | CH$_3$ |
| Ia.021 | Cl | Cl | Cl | CH$_3$ |
| Ia.022 | H | Cl | Br | CH$_3$ |
| Ia.023 | F | Cl | Br | CH$_3$ |
| Ia.024 | Cl | Cl | Br | CH$_3$ |
| Ia.025 | H | Cl | F | CH$_3$ |
| Ia.026 | F | Cl | F | CH$_3$ |
| Ia.027 | Cl | Cl | F | CH$_3$ |
| Ia.028 | H | Cl | I | CH$_3$ |
| Ia.029 | F | Cl | I | CH$_3$ |
| Ia.030 | Cl | Cl | I | CH$_3$ |
| Ia.031 | H | Cl | NO$_2$ | CH$_3$ |
| Ia.032 | F | Cl | NO$_2$ | CH$_3$ |
| Ia.033 | Cl | Cl | NO$_2$ | CH$_3$ |
| Ia.034 | H | Cl | CN | CH$_3$ |
| Ia.035 | F | Cl | CN | CH$_3$ |
| Ia.036 | Cl | Cl | CN | CH$_3$ |
| Ia.037 | H | Cl | Cl | CH$_2$CH$_3$ |
| Ia.038 | F | Cl | Cl | CH$_2$CH$_3$ |
| Ia.039 | Cl | Cl | Cl | CH$_2$CH$_3$ |
| Ia.040 | H | Cl | Br | CH$_2$CH$_3$ |
| Ia.041 | F | Cl | Br | CH$_2$CH$_3$ |
| Ia.042 | Cl | Cl | Br | CH$_2$CH$_3$ |
| Ia.043 | H | Cl | F | CH$_2$CH$_3$ |
| Ia.044 | F | Cl | F | CH$_2$CH$_3$ |
| Ia.045 | Cl | Cl | F | CH$_2$CH$_3$ |
| Ia.046 | H | Cl | I | CH$_2$CH$_3$ |
| Ia.047 | F | Cl | I | CH$_2$CH$_3$ |
| Ia.048 | Cl | Cl | I | CH$_2$CH$_3$ |
| Ia.049 | H | Cl | NO$_2$ | CH$_2$CH$_3$ |
| Ia.050 | F | Cl | NO$_2$ | CH$_2$CH$_3$ |
| Ia.051 | Cl | Cl | NO$_2$ | CH$_2$CH$_3$ |
| Ia.052 | H | Cl | CN | CH$_2$CH$_3$ |
| Ia.053 | F | Cl | CN | CH$_2$CH$_3$ |
| Ia.054 | Cl | Cl | CN | CH$_2$CH$_3$ |
| Ia.055 | H | Cl | Cl | CHCH$_2$CH$_3$ |
| Ia.056 | F | Cl | Cl | CHCH$_2$CH$_3$ |
| Ia.057 | Cl | Cl | Cl | CHCH$_2$CH$_3$ |
| Ia.058 | H | Cl | Br | CHCH$_2$CH$_3$ |
| Ia.059 | F | Cl | Br | CHCH$_2$CH$_3$ |
| Ia.060 | Cl | Cl | Br | CHCH$_2$CH$_3$ |
| Ia.061 | H | Cl | F | CHCH$_2$CH$_3$ |
| Ia.062 | F | Cl | F | CHCH$_2$CH$_3$ |
| Ia.063 | Cl | Cl | F | CHCH$_2$CH$_3$ |
| Ia.064 | H | Cl | I | CHCH$_2$CH$_3$ |
| Ia.065 | F | Cl | I | CHCH$_2$CH$_3$ |
| Ia.066 | Cl | Cl | I | CHCH$_2$CH$_3$ |
| Ia.067 | H | Cl | NO$_2$ | CHCH$_2$CH$_3$ |
| Ia.068 | F | Cl | NO$_2$ | CHCH$_2$CH$_3$ |
| Ia.069 | Cl | Cl | NO$_2$ | CHCH$_2$CH$_3$ |
| Ia.070 | H | Cl | CN | CHCH$_2$CH$_3$ |
| Ia.071 | F | Cl | CN | CHCH$_2$CH$_3$ |
| Ia.072 | Cl | Cl | CN | CHCH$_2$CH$_3$ |
| Ia.073 | H | Cl | Cl | CH(CH$_3$)$_2$ |
| Ia.074 | F | Cl | Cl | CH(CH$_3$)$_2$ |
| Ia.075 | Cl | Cl | Cl | CH(CH$_3$)$_2$ |
| Ia.076 | H | Cl | Br | CH(CH$_3$)$_2$ |
| Ia.077 | F | Cl | Br | CH(CH$_3$)$_2$ |
| Ia.078 | Cl | Cl | Br | CH(CH$_3$)$_2$ |
| Ia.079 | H | Cl | F | CH(CH$_3$)$_2$ |
| Ia.080 | F | Cl | F | CH(CH$_3$)$_2$ |
| Ia.081 | Cl | Cl | F | CH(CH$_3$)$_2$ |
| Ia.082 | H | Cl | I | CH(CH$_3$)$_2$ |
| Ia.083 | F | Cl | I | CH(CH$_3$)$_2$ |
| Ia.084 | Cl | Cl | I | CH(CH$_3$)$_2$ |
| Ia.085 | H | Cl | NO$_2$ | CH(CH$_3$)$_2$ |
| Ia.086 | F | Cl | NO$_2$ | CH(CH$_3$)$_2$ |
| Ia.087 | Cl | Cl | NO$_2$ | CH(CH$_3$)$_2$ |
| Ia.088 | H | Cl | CN | CH(CH$_3$)$_2$ |
| Ia.089 | F | Cl | CN | CH(CH$_3$)$_2$ |
| Ia.090 | Cl | Cl | CN | CH(CH$_3$)$_2$ |
| Ia.091 | H | Cl | Cl | CH$_2$CH$_2$CH$_2$CH$_3$ |
| Ia.092 | F | Cl | Cl | CH$_2$CH$_2$CH$_2$CH$_3$ |
| Ia.093 | Cl | Cl | Cl | CH$_2$CH$_2$CH$_2$CH$_3$ |
| Ia.094 | H | Cl | Br | CH$_2$CH$_2$CH$_2$CH$_3$ |
| Ia.095 | F | Cl | Br | CH$_2$CH$_2$CH$_2$CH$_3$ |
| Ia.096 | Cl | Cl | Br | CH$_2$CH$_2$CH$_2$CH$_3$ |
| Ia.097 | H | Cl | F | CH$_2$CH$_2$CH$_2$CH$_3$ |
| Ia.098 | F | Cl | F | CH$_2$CH$_2$CH$_2$CH$_3$ |
| Ia.099 | Cl | Cl | F | CH$_2$CH$_2$CH$_2$CH$_3$ |
| Ia.100 | H | Cl | I | CH$_2$CH$_2$CH$_2$CH$_3$ |
| Ia.101 | F | Cl | I | CH$_2$CH$_2$CH$_2$CH$_3$ |
| Ia.102 | Cl | Cl | I | CH$_2$CH$_2$CH$_2$CH$_3$ |
| Ia.103 | H | Cl | NO$_2$ | CH$_2$CH$_2$CH$_2$CH$_3$ |
| Ia.104 | F | Cl | NO$_2$ | CH$_2$CH$_2$CH$_2$CH$_3$ |
| Ia.105 | Cl | Cl | NO$_2$ | CH$_2$CH$_2$CH$_2$CH$_3$ |
| Ia.106 | H | Cl | CN | CH$_2$CH$_2$CH$_2$CH$_3$ |
| Ia.107 | F | Cl | CN | CH$_2$CH$_2$CH$_2$CH$_3$ |
| Ia.108 | Cl | Cl | CN | CH$_2$CH$_2$CH$_2$CH$_3$ |
| Ia.109 | H | Cl | Cl | CH$_2$CH(CH$_3$)$_2$ |
| Ia.110 | F | Cl | Cl | CH$_2$CH(CH$_3$)$_2$ |
| Ia.111 | Cl | Cl | Cl | CH$_2$CH(CH$_3$)$_2$ |
| Ia.112 | H | Cl | Br | CH$_2$CH(CH$_3$)$_2$ |
| Ia.113 | F | Cl | Br | CH$_2$CH(CH$_3$)$_2$ |
| Ia.114 | Cl | Cl | Br | CH$_2$CH(CH$_3$)$_2$ |
| Ia.115 | H | Cl | F | CH$_2$CH(CH$_3$)$_2$ |

TABLE 2-continued

Ia

| No. | R³ | R⁴ | R⁵ | R⁷ |
|---|---|---|---|---|
| Ia.116 | F | Cl | F | $CH_2CH(CH_3)_2$ |
| Ia.117 | Cl | Cl | F | $CH_2CH(CH_3)_2$ |
| Ia.118 | H | Cl | I | $CH_2CH(CH_3)_2$ |
| Ia.119 | F | Cl | I | $CH_2CH(CH_3)_2$ |
| Ia.120 | Cl | Cl | I | $CH_2CH(CH_3)_2$ |
| Ia.121 | H | Cl | $NO_2$ | $CH_2CH(CH_3)_2$ |
| Ia.122 | F | Cl | $NO_2$ | $CH_2CH(CH_3)_2$ |
| Ia.123 | Cl | Cl | $NO_2$ | $CH_2CH(CH_3)_2$ |
| Ia.124 | H | Cl | CN | $CH_2CH(CH_3)_2$ |
| Ia.125 | F | Cl | CN | $CH_2CH(CH_3)_2$ |
| Ia.126 | Cl | Cl | CN | $CH_2CH(CH_3)_2$ |
| Ia.127 | H | Cl | Cl | $CH(CH_3)CH_2CH_3$ |
| Ia.128 | F | Cl | Cl | $CH(CH_3)CH_2CH_3$ |
| Ia.129 | Cl | Cl | Cl | $CH(CH_3)CH_2CH_3$ |
| Ia.130 | H | Cl | Br | $CH(CH_3)CH_2CH_3$ |
| Ia.131 | F | Cl | Br | $CH(CH_3)CH_2CH_3$ |
| Ia.132 | Cl | Cl | Br | $CH(CH_3)CH_2CH_3$ |
| Ia.133 | H | Cl | F | $CH(CH_3)CH_2CH_3$ |
| Ia.134 | F | Cl | F | $CH(CH_3)CH_2CH_3$ |
| Ia.135 | Cl | Cl | F | $CH(CH_3)CH_2CH_3$ |
| Ia.136 | H | Cl | I | $CH(CH_3)CH_2CH_3$ |
| Ia.137 | F | Cl | I | $CH(CH_3)CH_2CH_3$ |
| Ia.138 | Cl | Cl | I | $CH(CH_3)CH_2CH_3$ |
| Ia.139 | H | Cl | $NO_2$ | $CH(CH_3)CH_2CH_3$ |
| Ia.140 | F | Cl | $NO_2$ | $CH(CH_3)CH_2CH_3$ |
| Ia.141 | Cl | Cl | $NO_2$ | $CH(CH_3)CH_2CH_3$ |
| Ia.142 | H | Cl | CN | $CH(CH_3)CH_2CH_3$ |
| Ia.143 | F | Cl | CN | $CH(CH_3)CH_2CH_3$ |
| Ia.144 | Cl | Cl | CN | $CH(CH_3)CH_2CH_3$ |
| Ia.145 | H | Cl | Cl | $C(CH_3)_3$ |
| Ia.146 | F | Cl | Cl | $C(CH_3)_3$ |
| Ia.147 | Cl | Cl | Cl | $C(CH_3)_3$ |
| Ia.148 | H | Cl | Br | $C(CH_3)_3$ |
| Ia.149 | F | Cl | Br | $C(CH_3)_3$ |
| Ia.150 | Cl | Cl | Br | $C(CH_3)_3$ |
| Ia.151 | H | Cl | F | $C(CH_3)_3$ |
| Ia.152 | F | Cl | F | $C(CH_3)_3$ |
| Ia.153 | Cl | Cl | F | $C(CH_3)_3$ |
| Ia.154 | H | Cl | I | $C(CH_3)_3$ |
| Ia.155 | F | Cl | I | $C(CH_3)_3$ |
| Ia.156 | Cl | Cl | I | $C(CH_3)_3$ |
| Ia.157 | H | Cl | $NO_2$ | $C(CH_3)_3$ |
| Ia.158 | F | Cl | $NO_2$ | $C(CH_3)_3$ |
| Ia.159 | Cl | Cl | $NO_2$ | $C(CH_3)_3$ |
| Ia.160 | H | Cl | CN | $C(CH_3)_3$ |
| Ia.161 | F | Cl | CN | $C(CH_3)_3$ |
| Ia.162 | Cl | Cl | CN | $C(CH_3)_3$ |
| Ia.163 | H | Cl | Cl | $CH_2CH_2CH_2CH_2CH_3$ |
| Ia.164 | F | Cl | Cl | $CH_2CH_2CH_2CH_2CH_3$ |
| Ia.165 | Cl | Cl | Cl | $CH_2CH_2CH_2CH_2CH_3$ |
| Ia.166 | H | Cl | Br | $CH_2CH_2CH_2CH_2CH_3$ |
| Ia.167 | F | Cl | Br | $CH_2CH_2CH_2CH_2CH_3$ |
| Ia.168 | Cl | Cl | Br | $CH_2CH_2CH_2CH_2CH_3$ |
| Ia.169 | H | Cl | F | $CH_2CH_2CH_2CH_2CH_3$ |
| Ia.170 | F | Cl | F | $CH_2CH_2CH_2CH_2CH_3$ |
| Ia.171 | Cl | Cl | F | $CH_2CH_2CH_2CH_2CH_3$ |
| Ia.172 | H | Cl | I | $CH_2CH_2CH_2CH_2CH_3$ |
| Ia.173 | F | Cl | I | $CH_2CH_2CH_2CH_2CH_3$ |
| Ia.174 | Cl | Cl | I | $CH_2CH_2CH_2CH_2CH_3$ |
| Ia.175 | H | Cl | $NO_2$ | $CH_2CH_2CH_2CH_2CH_3$ |
| Ia.176 | F | Cl | $NO_2$ | $CH_2CH_2CH_2CH_2CH_3$ |
| Ia.177 | Cl | Cl | $NO_2$ | $CH_2CH_2CH_2CH_2CH_3$ |
| Ia.178 | H | Cl | CN | $CH_2CH_2CH_2CH_2CH_3$ |
| Ia.179 | F | Cl | CN | $CH_2CH_2CH_2CH_2CH_3$ |
| Ia.180 | Cl | Cl | CN | $CH_2CH_2CH_2CH_2CH_3$ |
| Ia.181 | H | Cl | Cl | $CH_2CH_2CH_2CH_2CH_2CH_3$ |
| Ia.182 | F | Cl | Cl | $CH_2CH_2CH_2CH_2CH_2CH_3$ |
| Ia.183 | Cl | Cl | Cl | $CH_2CH_2CH_2CH_2CH_2CH_3$ |
| Ia.184 | H | Cl | Br | $CH_2CH_2CH_2CH_2CH_2CH_3$ |
| Ia.185 | F | Cl | Br | $CH_2CH_2CH_2CH_2CH_2CH_3$ |
| Ia.186 | Cl | Cl | Br | $CH_2CH_2CH_2CH_2CH_2CH_3$ |
| Ia.187 | H | Cl | F | $CH_2CH_2CH_2CH_2CH_2CH_3$ |
| Ia.188 | F | Cl | F | $CH_2CH_2CH_2CH_2CH_2CH_3$ |
| Ia.189 | Cl | Cl | F | $CH_2CH_2CH_2CH_2CH_2CH_3$ |
| Ia.190 | H | Cl | I | $CH_2CH_2CH_2CH_2CH_2CH_3$ |
| Ia.191 | F | Cl | I | $CH_2CH_2CH_2CH_2CH_2CH_3$ |
| Ia.192 | Cl | Cl | I | $CH_2CH_2CH_2CH_2CH_2CH_3$ |
| Ia.193 | H | Cl | $NO_2$ | $CH_2CH_2CH_2CH_2CH_2CH_3$ |
| Ia.194 | F | Cl | $NO_2$ | $CH_2CH_2CH_2CH_2CH_2CH_3$ |
| Ia.195 | Cl | Cl | $NO_2$ | $CH_2CH_2CH_2CH_2CH_2CH_3$ |
| Ia.196 | H | Cl | CN | $CH_2CH_2CH_2CH_2CH_2CH_3$ |
| Ia.197 | F | Cl | CN | $CH_2CH_2CH_2CH_2CH_2CH_3$ |
| Ia.198 | Cl | Cl | CN | $CH_2CH_2CH_2CH_2CH_2CH_3$ |
| Ia.199 | H | Cl | Cl | $CH_2-CH=CH_2$ |
| Ia.200 | F | Cl | Cl | $CH_2-CH=CH_2$ |
| Ia.201 | Cl | Cl | Cl | $CH_2-CH=CH_2$ |
| Ia.202 | H | Cl | Br | $CH_2-CH=CH_2$ |
| Ia.203 | F | Cl | Br | $CH_2-CH=CH_2$ |
| Ia.204 | Cl | Cl | Br | $CH_2-CH=CH_2$ |
| Ia.205 | H | Cl | F | $CH_2-CH=CH_2$ |
| Ia.206 | F | Cl | F | $CH_2-CH=CH_2$ |
| Ia.207 | Cl | Cl | F | $CH_2-CH=CH_2$ |
| Ia.208 | H | Cl | I | $CH_2-CH=CH_2$ |
| Ia.209 | F | Cl | I | $CH_2-CH=CH_2$ |
| Ia.210 | Cl | Cl | I | $CH_2-CH=CH_2$ |
| Ia.211 | H | Cl | CN | $CH_2-CH=CH_2$ |
| Ia.212 | F | Cl | CN | $CH_2-CH=CH_2$ |
| Ia.213 | Cl | Cl | CN | $CH_2-CH=CH_2$ |
| Ia.214 | H | Cl | $NO_2$ | $CH_2-CH=CH_2$ |
| Ia.215 | F | Cl | $NO_2$ | $CH_2-CH=CH_2$ |
| Ia.216 | Cl | Cl | $NO_2$ | $CH_2-CH=CH_2$ |
| Ia.217 | H | Cl | Cl | $CH(CH_3)CH=CH_2$ |
| Ia.218 | F | Cl | Cl | $CH(CH_3)CH=CH_2$ |
| Ia.219 | Cl | Cl | Cl | $CH(CH_3)CH=CH_2$ |
| Ia.220 | H | Cl | Br | $CH(CH_3)CH=CH_2$ |
| Ia.221 | F | Cl | Br | $CH(CH_3)CH=CH_2$ |
| Ia.222 | Cl | Cl | Br | $CH(CH_3)CH=CH_2$ |
| Ia.223 | H | Cl | F | $CH(CH_3)CH=CH_2$ |
| Ia.224 | F | Cl | F | $CH(CH_3)CH=CH_2$ |
| Ia.225 | Cl | Cl | F | $CH(CH_3)CH=CH_2$ |
| Ia.226 | H | Cl | I | $CH(CH_3)CH=CH_2$ |
| Ia.227 | F | Cl | I | $CH(CH_3)CH=CH_2$ |
| Ia.228 | Cl | Cl | I | $CH(CH_3)CH=CH_2$ |
| Ia.229 | H | Cl | $NO_2$ | $CH(CH_3)CH=CH_2$ |
| Ia.230 | F | Cl | $NO_2$ | $CH(CH_3)CH=CH_2$ |
| Ia.231 | Cl | Cl | $NO_2$ | $CH(CH_3)CH=CH_2$ |
| Ia.232 | H | Cl | CN | $CH(CH_3)CH=CH_2$ |
| Ia.233 | F | Cl | CN | $CH(CH_3)CH=CH_2$ |
| Ia.234 | Cl | Cl | CN | $CH(CH_3)CH=CH_2$ |
| Ia.235 | H | Cl | Cl | $CH_2C\equiv CH$ |
| Ia.236 | F | Cl | Cl | $CH_2C\equiv CH$ |
| Ia.237 | Cl | Cl | Cl | $CH_2C\equiv CH$ |
| Ia.238 | H | Cl | Br | $CH_2C\equiv CH$ |
| Ia.239 | F | Cl | Br | $CH_2C\equiv CH$ |
| Ia.240 | Cl | Cl | Br | $CH_2C\equiv CH$ |

TABLE 2-continued

Ia

| No. | R³ | R⁴ | R⁵ | R⁷ |
|---|---|---|---|---|
| Ia.241 | H | Cl | F | $CH_2C\equiv CH$ |
| Ia.242 | F | Cl | F | $CH_2C\equiv CH$ |
| Ia.243 | Cl | Cl | F | $CH_2C\equiv CH$ |
| Ia.244 | H | Cl | I | $CH_2C\equiv CH$ |
| Ia.245 | F | Cl | I | $CH_2C\equiv CH$ |
| Ia.246 | Cl | Cl | I | $CH_2C\equiv CH$ |
| Ia.247 | H | Cl | $NO_2$ | $CH_2C\equiv CH$ |
| Ia.248 | F | Cl | $NO_2$ | $CH_2C\equiv CH$ |
| Ia.249 | Cl | Cl | $NO_2$ | $CH_2C\equiv CH$ |
| Ia.250 | H | Cl | CN | $CH_2C\equiv CH$ |
| Ia.251 | F | Cl | CN | $CH_2C\equiv CH$ |
| Ia.252 | Cl | Cl | CN | $CH_2C\equiv CH$ |
| Ia.253 | H | Cl | Cl | $CH(CH_3)C\equiv CH$ |
| Ia.254 | F | Cl | Cl | $CH(CH_3)C\equiv CH$ |
| Ia.255 | Cl | Cl | Cl | $CH(CH_3)C\equiv CH$ |
| Ia.256 | H | Cl | Br | $CH(CH_3)C\equiv CH$ |
| Ia.257 | F | Cl | Br | $CH(CH_3)C\equiv CH$ |
| Ia.258 | Cl | Cl | Br | $CH(CH_3)C\equiv CH$ |
| Ia.259 | H | Cl | F | $CH(CH_3)C\equiv CH$ |
| Ia.260 | F | Cl | F | $CH(CH_3)C\equiv CH$ |
| Ia.261 | Cl | Cl | F | $CH(CH_3)C\equiv CH$ |
| Ia.262 | H | Cl | I | $CH(CH_3)C\equiv CH$ |
| Ia.263 | F | Cl | I | $CH(CH_3)C\equiv CH$ |
| Ia.264 | Cl | Cl | I | $CH(CH_3)C\equiv CH$ |
| Ia.265 | H | Cl | $NO_2$ | $CH(CH_3)C\equiv CH$ |
| Ia.266 | F | Cl | $NO_2$ | $CH(CH_3)C\equiv CH$ |
| Ia.267 | Cl | Cl | $NO_2$ | $CH(CH_3)C\equiv CH$ |
| Ia.268 | H | Cl | CN | $CH(CH_3)C\equiv CH$ |
| Ia.269 | F | Cl | CN | $CH(CH_3)C\equiv CH$ |
| Ia.270 | Cl | Cl | CN | $CH(CH_3)C\equiv CH$ |
| Ia.271 | H | Cl | Cl | Cyclopropyl |
| Ia.272 | F | Cl | Cl | Cyclopropyl |
| Ia.273 | Cl | Cl | Cl | Cyclopropyl |
| Ia.274 | H | Cl | Br | Cyclopropyl |
| Ia.275 | F | Cl | Br | Cyclopropyl |
| Ia.276 | Cl | Cl | Br | Cyclopropyl |
| Ia.277 | H | Cl | F | Cyclopropyl |
| Ia.278 | F | Cl | F | Cyclopropyl |
| Ia.279 | Cl | Cl | F | Cyclopropyl |
| Ia.280 | H | Cl | I | Cyclopropyl |
| Ia.281 | F | Cl | I | Cyclopropyl |
| Ia.282 | Cl | Cl | I | Cyclopropyl |
| Ia.283 | H | Cl | $NO_2$ | Cyclopropyl |
| Ia.284 | F | Cl | $NO_2$ | Cyclopropyl |
| Ia.285 | Cl | Cl | $NO_2$ | Cyclopropyl |
| Ia.286 | H | Cl | CN | Cyclopropyl |
| Ia.287 | F | Cl | CN | Cyclopropyl |
| Ia.288 | Cl | Cl | CN | Cyclopropyl |
| Ia.289 | H | Cl | Cl | Cyclopentyl |
| Ia.290 | F | Cl | Cl | Cyclopentyl |
| Ia.291 | Cl | Cl | Cl | Cyclopentyl |
| Ia.292 | H | Cl | Br | Cyclopentyl |
| Ia.293 | F | Cl | Br | Cyclopentyl |
| Ia.294 | Cl | Cl | Br | Cyclopentyl |
| Ia.295 | H | Cl | F | Cyclopentyl |
| Ia.296 | F | Cl | F | Cyclopentyl |
| Ia.297 | Cl | Cl | F | Cyclopentyl |
| Ia.298 | H | Cl | I | Cyclopentyl |
| Ia.299 | F | Cl | I | Cyclopentyl |
| Ia.300 | Cl | Cl | I | Cyclopentyl |
| Ia.301 | H | Cl | $NO_2$ | Cyclopentyl |
| Ia.302 | F | Cl | $NO_2$ | Cyclopentyl |
| Ia.303 | Cl | Cl | $NO_2$ | Cyclopentyl |
| Ia.304 | H | Cl | CN | Cyclopentyl |
| Ia.305 | F | Cl | CN | Cyclopentyl |
| Ia.306 | Cl | Cl | CN | Cyclopentyl |
| Ia.307 | H | Cl | Cl | Cyclohexyl |
| Ia.308 | F | Cl | Cl | Cyclohexyl |
| Ia.309 | Cl | Cl | Cl | Cyclohexyl |
| Ia.310 | H | Cl | Br | Cyclohexyl |
| Ia.311 | F | Cl | Br | Cyclohexyl |
| Ia.312 | Cl | Cl | Br | Cyclohexyl |
| Ia.313 | H | Cl | F | Cyclohexyl |
| Ia.314 | F | Cl | F | Cyclohexyl |
| Ia.315 | Cl | Cl | F | Cyclohexyl |
| Ia.316 | H | Cl | I | Cyclohexyl |
| Ia.317 | F | Cl | I | Cyclohexyl |
| Ia.318 | Cl | Cl | I | Cyclohexyl |
| Ia.319 | H | Cl | $NO_2$ | Cyclohexyl |
| Ia.320 | F | Cl | $NO_2$ | Cyclohexyl |
| Ia.321 | Cl | Cl | $NO_2$ | Cyclohexyl |
| Ia.322 | H | Cl | CN | Cyclohexyl |
| Ia.323 | F | Cl | CN | Cyclohexyl |
| Ia.324 | Cl | Cl | CN | Cyclohexyl |
| Ia.325 | H | Cl | Cl | $OCH_2CH_2F$ |
| Ia.326 | F | Cl | Cl | $OCH_2CH_2F$ |
| Ia.327 | Cl | Cl | Cl | $OCH_2CH_2F$ |
| Ia.328 | H | Cl | Br | $OCH_2CH_2F$ |
| Ia.329 | F | Cl | Br | $OCH_2CH_2F$ |
| Ia.330 | Cl | Cl | Br | $OCH_2CH_2F$ |
| Ia.331 | H | Cl | I | $OCH_2CH_2F$ |
| Ia.332 | F | Cl | I | $OCH_2CH_2F$ |
| Ia.333 | Cl | Cl | I | $OCH_2CH_2F$ |
| Ia.334 | H | Cl | F | $OCH_2CH_2F$ |
| Ia.335 | F | Cl | F | $OCH_2CH_2F$ |
| Ia.336 | Cl | Cl | F | $OCH_2CH_2F$ |
| Ia.337 | H | Cl | $NO_2$ | $OCH_2CH_2F$ |
| Ia.338 | F | Cl | $NO_2$ | $OCH_2CH_2F$ |
| Ia.339 | Cl | Cl | $NO_2$ | $OCH_2CH_2F$ |
| Ia.340 | H | Cl | CN | $OCH_2CH_2F$ |
| Ia.341 | F | Cl | CN | $OCH_2CH_2F$ |
| Ia.342 | Cl | Cl | CN | $OCH_2CH_2F$ |
| Ia.343 | H | Cl | Cl | $OCH_2CF_3$ |
| Ia.344 | F | Cl | Cl | $OCH_2CF_3$ |

TABLE 2-continued

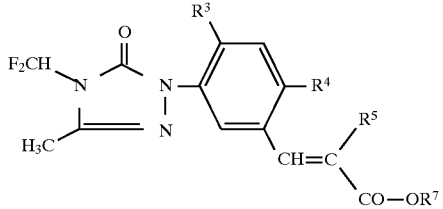

Ia

| No. | R³ | R⁴ | R⁵ | R⁷ |
|---|---|---|---|---|
| Ia.345 | Cl | Cl | Cl | OCH$_2$CF$_3$ |
| Ia.346 | H | Cl | Br | OCH$_2$CF$_3$ |
| Ia.347 | F | Cl | Br | OCH$_2$CF$_3$ |
| Ia.348 | Cl | Cl | Br | OCH$_2$CF$_3$ |
| Ia.349 | H | Cl | F | OCH$_2$CF$_3$ |
| Ia.350 | F | Cl | F | OCH$_2$CF$_3$ |
| Ia.351 | Cl | Cl | F | OCH$_2$CF$_3$ |
| Ia.352 | H | Cl | I | OCH$_2$CF$_3$ |
| Ia.353 | F | Cl | I | OCH$_2$CF$_3$ |
| Ia.354 | Cl | Cl | I | OCH$_2$CF$_3$ |
| Ia.355 | H | Cl | NO$_2$ | OCH$_2$CF$_3$ |
| Ia.356 | F | Cl | NO$_2$ | OCH$_2$CF$_3$ |
| Ia.357 | Cl | Cl | NO$_2$ | OCH$_2$CF$_3$ |
| Ia.358 | H | Cl | CN | OCH$_2$CF$_3$ |
| Ia.359 | F | Cl | CN | OCH$_2$CF$_3$ |
| Ia.360 | Cl | Cl | CN | OCH$_2$CF$_3$ |
| Ia.361 | H | Cl | Cl | CH$_2$CH$_2$Cl |
| Ia.362 | F | Cl | Cl | CH$_2$CH$_2$Cl |
| Ia.363 | Cl | Cl | Cl | CH$_2$CH$_2$Cl |
| Ia.364 | H | Cl | Br | CH$_2$CH$_2$Cl |
| Ia.365 | F | Cl | Br | CH$_2$CH$_2$Cl |
| Ia.366 | Cl | Cl | Br | CH$_2$CH$_2$Cl |
| Ia.367 | H | Cl | F | CH$_2$CH$_2$Cl |
| Ia.368 | F | Cl | F | CH$_2$CH$_2$Cl |
| Ia.369 | Cl | Cl | F | CH$_2$CH$_2$Cl |
| Ia.370 | H | Cl | I | CH$_2$CH$_2$Cl |
| Ia.371 | F | Cl | I | CH$_2$CH$_2$Cl |
| Ia.372 | Cl | Cl | I | CH$_2$CH$_2$Cl |
| Ia.373 | H | Cl | NO$_2$ | CH$_2$CH$_2$Cl |
| Ia.374 | F | Cl | NO$_2$ | CH$_2$CH$_2$Cl |
| Ia.375 | Cl | Cl | NO$_2$ | CH$_2$CH$_2$Cl |
| Ia.376 | H | Cl | CN | CH$_2$CH$_2$Cl |
| Ia.377 | F | Cl | CN | CH$_2$CH$_2$Cl |
| Ia.378 | Cl | Cl | CN | CH$_2$CH$_2$Cl |
| Ia.379 | H | Cl | Cl | OCH$_2$CN |
| Ia.380 | F | Cl | Cl | OCH$_2$CN |
| Ia.381 | Cl | Cl | Cl | OCH$_2$CN |
| Ia.382 | H | Cl | Br | OCH$_2$CN |
| Ia.383 | F | Cl | Br | OCH$_2$CN |
| Ia.384 | Cl | Cl | Br | OCH$_2$CN |
| Ia.385 | H | Cl | F | OCH$_2$CN |
| Ia.386 | F | Cl | F | OCH$_2$CN |
| Ia.387 | Cl | Cl | F | OCH$_2$CN |
| Ia.388 | H | Cl | I | OCH$_2$CN |
| Ia.389 | F | Cl | I | OCH$_2$CN |
| Ia.390 | Cl | Cl | I | OCH$_2$CN |
| Ia.391 | H | Cl | NO$_2$ | OCH$_2$CN |
| Ia.392 | F | Cl | NO$_2$ | OCH$_2$CN |
| Ia.393 | Cl | Cl | NO$_2$ | OCH$_2$CN |
| Ia.394 | H | Cl | CN | OCH$_2$CN |
| Ia.395 | F | Cl | CN | OCH$_2$CN |
| Ia.396 | Cl | Cl | CN | OCH$_2$CN |
| Ia.397 | H | Cl | Cl | OCH(CH$_3$)CN |
| Ia.398 | F | Cl | Cl | OCH(CH$_3$)CN |
| Ia.399 | Cl | Cl | Cl | OCH(CH$_3$)CN |
| Ia.400 | H | Cl | Br | OCH(CH$_3$)CN |
| Ia.401 | F | Cl | Br | OCH(CH$_3$)CN |
| Ia.402 | Cl | Cl | Br | OCH(CH$_3$)CN |
| Ia.403 | H | Cl | F | OCH(CH$_3$)CN |
| Ia.404 | F | Cl | F | OCH(CH$_3$)CN |
| Ia.405 | Cl | Cl | F | OCH(CH$_3$)CN |
| Ia.406 | H | Cl | I | OCH(CH$_3$)CN |
| Ia.407 | F | Cl | I | OCH(CH$_3$)CN |
| Ia.408 | Cl | Cl | I | OCH(CH$_3$)CN |
| Ia.409 | H | Cl | CN | OCH(CH$_3$)CN |

TABLE 2-continued

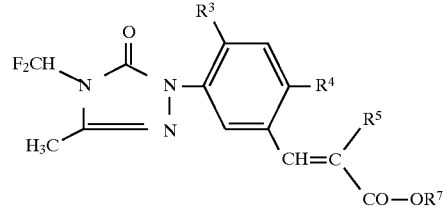

Ia

| No. | R³ | R⁴ | R⁵ | R⁷ |
|---|---|---|---|---|
| Ia.410 | F | Cl | CN | OCH(CH$_3$)CN |
| Ia.411 | Cl | Cl | CN | OCH(CH$_3$)CN |
| Ia.412 | H | Cl | NO$_2$ | OCH(CH$_3$)CN |
| Ia.413 | F | Cl | NO$_2$ | OCH(CH$_3$)CN |
| Ia.414 | Cl | Cl | NO$_2$ | OCH(CH$_3$)CN |
| Ia.415 | H | Cl | Cl | OCH$_2$CH$_2$OCH$_3$ |
| Ia.416 | F | Cl | Cl | OCH$_2$CH$_2$OCH$_3$ |
| Ia.417 | Cl | Cl | Cl | OCH$_2$CH$_2$OCH$_3$ |
| Ia.418 | H | Cl | Br | OCH$_2$CH$_2$OCH$_3$ |
| Ia.419 | F | Cl | Br | OCH$_2$CH$_2$OCH$_3$ |
| Ia.420 | Cl | Cl | Br | OCH$_2$CH$_2$OCH$_3$ |
| Ia.421 | H | Cl | F | OCH$_2$CH$_2$OCH$_3$ |
| Ia.422 | F | Cl | F | OCH$_2$CH$_2$OCH$_3$ |
| Ia.423 | Cl | Cl | F | OCH$_2$CH$_2$OCH$_3$ |
| Ia.424 | H | Cl | I | OCH$_2$CH$_2$OCH$_3$ |
| Ia.425 | F | Cl | I | OCH$_2$CH$_2$OCH$_3$ |
| Ia.426 | Cl | Cl | I | OCH$_2$CH$_2$OCH$_3$ |
| Ia.427 | H | Cl | NO$_2$ | OCH$_2$CH$_2$OCH$_3$ |
| Ia.428 | F | Cl | NO$_2$ | OCH$_2$CH$_2$OCH$_3$ |
| Ia.429 | Cl | Cl | NO$_2$ | OCH$_2$CH$_2$OCH$_3$ |
| Ia.430 | H | Cl | CN | OCH$_2$CH$_2$OCH$_3$ |
| Ia.431 | F | Cl | CN | OCH$_2$CH$_2$OCH$_3$ |
| Ia.432 | Cl | Cl | CN | OCH$_2$CH$_2$OCH$_3$ |
| Ia.433 | H | Cl | Cl | OCH$_2$CH$_2$OCH$_2$CH$_3$ |
| Ia.434 | F | Cl | Cl | OCH$_2$CH$_2$OCH$_2$CH$_3$ |
| Ia.435 | Cl | Cl | Cl | OCH$_2$CH$_2$OCH$_2$CH$_3$ |
| Ia.436 | H | Cl | Br | OCH$_2$CH$_2$OCH$_2$CH$_3$ |
| Ia.437 | F | Cl | Br | OCH$_2$CH$_2$OCH$_2$CH$_3$ |
| Ia.438 | Cl | Cl | Br | OCH$_2$CH$_2$OCH$_2$CH$_3$ |
| Ia.439 | H | Cl | F | OCH$_2$CH$_2$OCH$_2$CH$_3$ |
| Ia.440 | F | Cl | F | OCH$_2$CH$_2$OCH$_2$CH$_3$ |
| Ia.441 | Cl | Cl | F | OCH$_2$CH$_2$OCH$_2$CH$_3$ |
| Ia.442 | H | Cl | I | OCH$_2$CH$_2$OCH$_2$CH$_3$ |
| Ia.443 | F | Cl | I | OCH$_2$CH$_2$OCH$_2$CH$_3$ |
| Ia.444 | Cl | Cl | I | OCH$_2$CH$_2$OCH$_2$CH$_3$ |
| Ia.445 | H | Cl | NO$_2$ | OCH$_2$CH$_2$OCH$_2$CH$_3$ |
| Ia.446 | F | Cl | NO$_2$ | OCH$_2$CH$_2$OCH$_2$CH$_3$ |
| Ia.447 | Cl | Cl | NO$_2$ | OCH$_2$CH$_2$OCH$_2$CH$_3$ |
| Ia.448 | H | Cl | CN | OCH$_2$CH$_2$OCH$_2$CH$_3$ |
| Ia.449 | F | Cl | CN | OCH$_2$CH$_2$OCH$_2$CH$_3$ |
| Ia.450 | Cl | Cl | CN | OCH$_2$CH$_2$OCH$_2$CH$_3$ |
| Ia.451 | H | Cl | Cl | CH$_2$CO$_2$CH$_3$ |
| Ia.452 | F | Cl | Cl | CH$_2$CO$_2$CH$_3$ |
| Ia.453 | Cl | Cl | Cl | CH$_2$CO$_2$CH$_3$ |
| Ia.454 | H | Cl | Br | CH$_2$CO$_2$CH$_3$ |
| Ia.455 | F | Cl | Br | CH$_2$CO$_2$CH$_3$ |
| Ia.456 | Cl | Cl | Br | CH$_2$CO$_2$CH$_3$ |
| Ia.457 | H | Cl | F | CH$_2$CO$_2$CH$_3$ |
| Ia.458 | F | Cl | F | CH$_2$CO$_2$CH$_3$ |
| Ia.459 | Cl | Cl | F | CH$_2$CO$_2$CH$_3$ |
| Ia.460 | H | Cl | I | CH$_2$CO$_2$CH$_3$ |
| Ia.461 | F | Cl | I | CH$_2$CO$_2$CH$_3$ |
| Ia.462 | Cl | Cl | I | CH$_2$CO$_2$CH$_3$ |
| Ia.463 | H | Cl | NO$_2$ | CH$_2$CO$_2$CH$_3$ |
| Ia.464 | F | Cl | NO$_2$ | CH$_2$CO$_2$CH$_3$ |
| Ia.465 | Cl | Cl | NO$_2$ | CH$_2$CO$_2$CH$_3$ |
| Ia.466 | H | Cl | CN | CH$_2$CO$_2$CH$_3$ |
| Ia.467 | F | Cl | CN | CH$_2$CO$_2$CH$_3$ |
| Ia.468 | Cl | Cl | CN | CH$_2$CO$_2$CH$_3$ |
| Ia.469 | H | Cl | Cl | CH$_2$CO$_2$CH$_2$CH$_3$ |
| Ia.470 | F | Cl | Cl | CH$_2$CO$_2$CH$_2$CH$_3$ |
| Ia.471 | Cl | Cl | Cl | CH$_2$CO$_2$CH$_2$CH$_3$ |
| Ia.472 | H | Cl | Br | CH$_2$CO$_2$CH$_2$CH$_3$ |
| Ia.473 | F | Cl | Br | CH$_2$CO$_2$CH$_2$CH$_3$ |
| Ia.474 | Cl | Cl | Br | CH$_2$CO$_2$CH$_2$CH$_3$ |

TABLE 2-continued

Ia

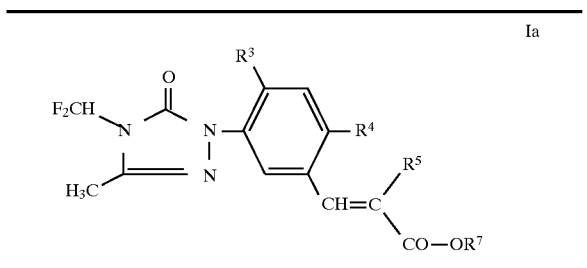 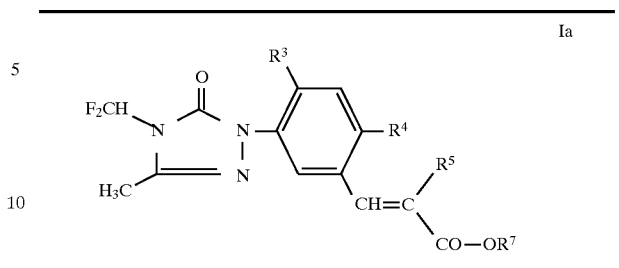

| No. | R³ | R⁴ | R⁵ | R⁷ |
|---|---|---|---|---|
| Ia.475 | H | Cl | F | $CH_2CO_2CH_2CH_3$ |
| Ia.476 | F | Cl | F | $CH_2CO_2CH_2CH_3$ |
| Ia.477 | Cl | Cl | F | $CH_2CO_2CH_2CH_3$ |
| Ia.478 | H | Cl | I | $CH_2CO_2CH_2CH_3$ |
| Ia.479 | F | Cl | I | $CH_2CO_2CH_2CH_3$ |
| Ia.480 | Cl | Cl | I | $CH_2CO_2CH_2CH_3$ |
| Ia.481 | H | Cl | $NO_2$ | $CH_2CO_2CH_2CH_3$ |
| Ia.482 | F | Cl | $NO_2$ | $CH_2CO_2CH_2CH_3$ |
| Ia.483 | Cl | Cl | $NO_2$ | $CH_2CO_2CH_2CH_3$ |
| Ia.484 | H | Cl | CN | $CH_2CO_2CH_2CH_3$ |
| Ia.485 | F | Cl | CN | $CH_2CO_2CH_2CH_3$ |
| Ia.486 | Cl | Cl | CN | $CH_2CO_2CH_2CH_3$ |
| Ia.487 | H | Cl | Cl | $CH_2CO_2CH(CH_3)_2$ |
| Ia.488 | F | Cl | Cl | $CH_2CO_2CH(CH_3)_2$ |
| Ia.489 | Cl | Cl | Cl | $CH_2CO_2CH(CH_3)_2$ |
| Ia.490 | H | Cl | Br | $CH_2CO_2CH(CH_3)_2$ |
| Ia.491 | F | Cl | Br | $CH_2CO_2CH(CH_3)_2$ |
| Ia.492 | Cl | Cl | Br | $CH_2CO_2CH(CH_3)_2$ |
| Ia.493 | H | Cl | F | $CH_2CO_2CH(CH_3)_2$ |
| Ia.494 | F | Cl | F | $CH_2CO_2CH(CH_3)_2$ |
| Ia.495 | Cl | Cl | F | $CH_2CO_2CH(CH_3)_2$ |
| Ia.496 | H | Cl | I | $CH_2CO_2CH(CH_3)_2$ |
| Ia.497 | F | Cl | I | $CH_2CO_2CH(CH_3)_2$ |
| Ia.498 | Cl | Cl | I | $CH_2CO_2CH(CH_3)_2$ |
| Ia.499 | H | Cl | $NO_2$ | $CH_2CO_2CH(CH_3)_2$ |
| Ia.500 | F | Cl | $NO_2$ | $CH_2CO_2CH(CH_3)_2$ |
| Ia.501 | Cl | Cl | $NO_2$ | $CH_2CO_2CH(CH_3)_2$ |
| Ia.502 | H | Cl | CN | $CH_2CO_2CH(CH_3)_2$ |
| Ia.503 | F | Cl | CN | $CH_2CO_2CH(CH_3)_2$ |
| Ia.504 | Cl | Cl | CN | $CH_2CO_2CH(CH_3)_2$ |
| Ia.505 | H | Cl | Cl | $CH(CH_3)CO_2CH_3$ |
| Ia.506 | F | Cl | Cl | $CH(CH_3)CO_2CH_3$ |
| Ia.507 | Cl | Cl | Cl | $CH(CH_3)CO_2CH_3$ |
| Ia.508 | H | Cl | Br | $CH(CH_3)CO_2CH_3$ |
| Ia.509 | F | Cl | Br | $CH(CH_3)CO_2CH_3$ |
| Ia.510 | Cl | Cl | Br | $CH(CH_3)CO_2CH_3$ |
| Ia.511 | H | Cl | F | $CH(CH_3)CO_2CH_3$ |
| Ia.512 | F | Cl | F | $CH(CH_3)CO_2CH_3$ |
| Ia.513 | Cl | Cl | F | $CH(CH_3)CO_2CH_3$ |
| Ia.514 | H | Cl | I | $CH(CH_3)CO_2CH_3$ |
| Ia.515 | F | Cl | I | $CH(CH_3)CO_2CH_3$ |
| Ia.516 | Cl | Cl | I | $CH(CH_3)CO_2CH_3$ |
| Ia.517 | H | Cl | $NO_2$ | $CH(CH_3)CO_2CH_3$ |
| Ia.518 | F | Cl | $NO_2$ | $CH(CH_3)CO_2CH_3$ |
| Ia.519 | Cl | Cl | $NO_2$ | $CH(CH_3)CO_2CH_3$ |
| Ia.520 | H | Cl | CN | $CH(CH_3)CO_2CH_3$ |
| Ia.521 | F | Cl | CN | $CH(CH_3)CO_2CH_3$ |
| Ia.522 | Cl | Cl | CN | $CH(CH_3)CO_2CH_3$ |
| Ia.523 | H | Cl | Cl | $CH(CH_3)CO_2CH_2CH_3$ |
| Ia.524 | F | Cl | Cl | $CH(CH_3)CO_2CH_2CH_3$ |
| Ia.525 | Cl | Cl | Cl | $CH(CH_3)CO_2CH_2CH_3$ |
| Ia.526 | H | Cl | Br | $CH(CH_3)CO_2CH_2CH_3$ |
| Ia.527 | F | Cl | Br | $CH(CH_3)CO_2CH_2CH_3$ |
| Ia.528 | Cl | Cl | Br | $CH(CH_3)CO_2CH_2CH_3$ |
| Ia.529 | H | Cl | F | $CH(CH_3)CO_2CH_2CH_3$ |
| Ia.530 | F | Cl | F | $CH(CH_3)CO_2CH_2CH_3$ |
| Ia.531 | Cl | Cl | F | $CH(CH_3)CO_2CH_2CH_3$ |
| Ia.532 | H | Cl | I | $CH(CH_3)CO_2CH_2CH_3$ |
| Ia.533 | F | Cl | I | $CH(CH_3)CO_2CH_2CH_3$ |
| Ia.534 | Cl | Cl | I | $CH(CH_3)CO_2CH_2CH_3$ |
| Ia.535 | H | Cl | CN | $CH(CH_3)CO_2CH_2CH_3$ |
| Ia.536 | F | Cl | CN | $CH(CH_3)CO_2CH_2CH_3$ |
| Ia.537 | Cl | Cl | CN | $CH(CH_3)CO_2CH_2CH_3$ |
| Ia.538 | H | Cl | $NO_2$ | $CH(CH_3)CO_2CH_2CH_3$ |
| Ia.539 | F | Cl | $NO_2$ | $CH(CH_3)CO_2CH_2CH_3$ |
| Ia.540 | Cl | Cl | $NO_2$ | $CH(CH_3)CO_2CH_2CH_3$ |
| Ia.541 | H | Cl | Cl | $CH(CH_2CH_3)CO_2CH_3$ |
| Ia.542 | F | Cl | Cl | $CH(CH_2CH_3)CO_2CH_3$ |
| Ia.543 | Cl | Cl | Cl | $CH(CH_2CH_3)CO_2CH_3$ |
| Ia.544 | H | Cl | Br | $CH(CH_2CH_3)CO_2CH_3$ |
| Ia.545 | F | Cl | Br | $CH(CH_2CH_3)CO_2CH_3$ |
| Ia.546 | Cl | Cl | Br | $CH(CH_2CH_3)CO_2CH_3$ |
| Ia.547 | H | Cl | F | $CH(CH_2CH_3)CO_2CH_3$ |
| Ia.548 | F | Cl | F | $CH(CH_2CH_3)CO_2CH_3$ |
| Ia.549 | Cl | Cl | F | $CH(CH_2CH_3)CO_2CH_3$ |
| Ia.550 | H | Cl | I | $CH(CH_2CH_3)CO_2CH_3$ |
| Ia.551 | F | Cl | I | $CH(CH_2CH_3)CO_2CH_3$ |
| Ia.552 | Cl | Cl | I | $CH(CH_2CH_3)CO_2CH_3$ |
| Ia.553 | H | Cl | $NO_2$ | $CH(CH_2CH_3)CO_2CH_3$ |
| Ia.554 | F | Cl | $NO_2$ | $CH(CH_2CH_3)CO_2CH_3$ |
| Ia.555 | Cl | Cl | $NO_2$ | $CH(CH_2CH_3)CO_2CH_3$ |
| Ia.556 | H | Cl | CN | $CH(CH_2CH_3)CO_2CH_3$ |
| Ia.557 | F | Cl | CN | $CH(CH_2CH_3)CO_2CH_3$ |
| Ia.558 | Cl | Cl | CN | $CH(CH_2CH_3)CO_2CH_3$ |
| Ia.559 | H | Cl | Cl | $CH(CH_2CH_3)CO_2CH_2CH_3$ |
| Ia.560 | F | Cl | Cl | $CH(CH_2CH_3)CO_2CH_2CH_3$ |
| Ia.561 | Cl | Cl | Cl | $CH(CH_2CH_3)CO_2CH_2CH_3$ |
| Ia.562 | H | Cl | Br | $CH(CH_2CH_3)CO_2CH_2CH_3$ |
| Ia.563 | F | Cl | Br | $CH(CH_2CH_3)CO_2CH_2CH_3$ |
| Ia.564 | Cl | Cl | Br | $CH(CH_2CH_3)CO_2CH_2CH_3$ |
| Ia.565 | H | Cl | F | $CH(CH_2CH_3)CO_2CH_2CH_3$ |
| Ia.566 | F | Cl | F | $CH(CH_2CH_3)CO_2CH_2CH_3$ |
| Ia.567 | Cl | Cl | F | $CH(CH_2CH_3)CO_2CH_2CH_3$ |
| Ia.568 | H | Cl | I | $CH(CH_2CH_3)CO_2CH_2CH_3$ |
| Ia.569 | F | Cl | I | $CH(CH_2CH_3)CO_2CH_2CH_3$ |
| Ia.570 | Cl | Cl | I | $CH(CH_2CH_3)CO_2CH_2CH_3$ |
| Ia.571 | H | Cl | $NO_2$ | $CH(CH_2CH_3)CO_2CH_2CH_3$ |
| Ia.572 | F | Cl | $NO_2$ | $CH(CH_2CH_3)CO_2CH_2CH_3$ |
| Ia.573 | Cl | Cl | $NO_2$ | $CH(CH_2CH_3)CO_2CH_2CH_3$ |
| Ia.574 | H | Cl | CN | $CH(CH_2CH_3)CO_2CH_2CH_3$ |
| Ia.575 | F | Cl | CN | $CH(CH_2CH_3)CO_2CH_2CH_3$ |
| Ia.576 | Cl | Cl | CN | $CH(CH_2CH_3)CO_2CH_2CH_3$ |
| Ia.577 | H | Cl | Cl | $CH_2CONHCH_3$ |
| Ia.578 | F | Cl | Cl | $CH_2CONHCH_3$ |
| Ia.579 | Cl | Cl | Cl | $CH_2CONHCH_3$ |
| Ia.580 | H | Cl | Br | $CH_2CONHCH_3$ |
| Ia.581 | F | Cl | Br | $CH_2CONHCH_3$ |
| Ia.582 | Cl | Cl | Br | $CH_2CONHCH_3$ |
| Ia.583 | H | Cl | F | $CH_2CONHCH_3$ |
| Ia.584 | F | Cl | F | $CH_2CONHCH_3$ |
| Ia.585 | Cl | Cl | F | $CH_2CONHCH_3$ |
| Ia.586 | H | Cl | I | $CH_2CONHCH_3$ |
| Ia.587 | F | Cl | I | $CH_2CONHCH_3$ |
| Ia.588 | Cl | Cl | I | $CH_2CONHCH_3$ |
| Ia.589 | H | Cl | $NO_2$ | $CH_2CONHCH_3$ |
| Ia.590 | F | Cl | $NO_2$ | $CH_2CONHCH_3$ |
| Ia.591 | Cl | Cl | $NO_2$ | $CH_2CONHCH_3$ |
| Ia.592 | H | Cl | CN | $CH_2CONHCH_3$ |
| Ia.593 | F | Cl | CN | $CH_2CONHCH_3$ |
| Ia.594 | Cl | Cl | CN | $CH_2CONHCH_3$ |
| Ia.595 | H | Cl | Cl | $CH_2CONHCH_2CH_3$ |
| Ia.596 | F | Cl | Cl | $CH_2CONHCH_2CH_3$ |
| Ia.597 | Cl | Cl | Cl | $CH_2CONHCH_2CH_3$ |
| Ia.598 | H | Cl | Br | $CH_2CONHCH_2CH_3$ |
| Ia.599 | F | Cl | Br | $CH_2CONHCH_2CH_3$ |
| Ia.600 | Cl | Cl | Br | $CH_2CONHCH_2CH_3$ |
| Ia.601 | H | Cl | F | $CH_2CONHCH_2CH_3$ |
| Ia.602 | F | Cl | F | $CH_2CONHCH_2CH_3$ |
| Ia.603 | Cl | Cl | F | $CH_2CONHCH_2CH_3$ |
| Ia.604 | H | Cl | I | $CH_2CONHCH_2CH_3$ |

TABLE 2-continued

Ia

| No. | R³ | R⁴ | R⁵ | R⁷ |
|---|---|---|---|---|
| Ia.605 | F | Cl | I | CH₂CONHCH₂CH₃ |
| Ia.606 | Cl | Cl | I | CH₂CONHCH₂CH₃ |
| Ia.607 | H | Cl | NO₂ | CH₂CONHCH₂CH₃ |
| Ia.608 | F | Cl | NO₂ | CH₂CONHCH₂CH₃ |
| Ia.609 | Cl | Cl | NO₂ | CH₂CONHCH₂CH₃ |
| Ia.610 | H | Cl | CN | CH₂CONHCH₂CH₃ |
| Ia.611 | F | Cl | CN | CH₂CONHCH₂CH₃ |
| Ia.612 | Cl | Cl | CN | CH₂CONHCH₂CH₃ |
| Ia.613 | H | Cl | Cl | CH(CH₃)CONHCH₃ |
| Ia.614 | F | Cl | Cl | CH(CH₃)CONHCH₃ |
| Ia.615 | Cl | Cl | Cl | CH(CH₃)CONHCH₃ |
| Ia.616 | H | Cl | Br | CH(CH₃)CONHCH₃ |
| Ia.617 | F | Cl | Br | CH(CH₃)CONHCH₃ |
| Ia.618 | Cl | Cl | Br | CH(CH₃)CONHCH₃ |
| Ia.619 | H | Cl | F | CH(CH₃)CONHCH₃ |
| Ia.620 | F | Cl | F | CH(CH₃)CONHCH₃ |
| Ia.621 | Cl | Cl | F | CH(CH₃)CONHCH₃ |
| Ia.622 | H | Cl | I | CH(CH₃)CONHCH₃ |
| Ia.623 | F | Cl | I | CH(CH₃)CONHCH₃ |
| Ia.624 | Cl | Cl | I | CH(CH₃)CONHCH₃ |
| Ia.625 | H | Cl | NO₂ | CH(CH₃)CONHCH₃ |
| Ia.626 | F | Cl | NO₂ | CH(CH₃)CONHCH₃ |
| Ia.627 | Cl | Cl | NO₂ | CH(CH₃)CONHCH₃ |
| Ia.628 | H | Cl | CN | CH(CH₃)CONHCH₃ |
| Ia.629 | F | Cl | CN | CH(CH₃)CONHCH₃ |
| Ia.630 | Cl | Cl | CN | CH(CH₃)CONHCH₃ |
| Ia.631 | H | Cl | Cl | CH(CH₂CH₃)CONHCH₃ |
| Ia.632 | F | Cl | Cl | CH(CH₂CH₃)CONHCH₃ |
| Ia.633 | Cl | Cl | Cl | CH(CH₂CH₃)CONHCH₃ |
| Ia.634 | H | Cl | Br | CH(CH₂CH₃)CONHCH₃ |
| Ia.635 | F | Cl | Br | CH(CH₂CH₃)CONHCH₃ |
| Ia.636 | Cl | Cl | Br | CH(CH₂CH₃)CONHCH₃ |
| Ia.637 | H | Cl | F | CH(CH₂CH₃)CONHCH₃ |
| Ia.638 | F | Cl | F | CH(CH₂CH₃)CONHCH₃ |
| Ia.639 | Cl | Cl | F | CH(CH₂CH₃)CONHCH₃ |
| Ia.640 | H | Cl | I | CH(CH₂CH₃)CONHCH₃ |
| Ia.641 | F | Cl | I | CH(CH₂CH₃)CONHCH₃ |
| Ia.642 | Cl | Cl | I | CH(CH₂CH₃)CONHCH₃ |
| Ia.643 | H | Cl | NO₂ | CH(CH₂CH₃)CONHCH₃ |
| Ia.644 | F | Cl | NO₂ | CH(CH₂CH₃)CONHCH₃ |
| Ia.645 | Cl | Cl | NO₂ | CH(CH₂CH₃)CONHCH₃ |
| Ia.646 | H | Cl | CN | CH(CH₂CH₃)CONHCH₃ |
| Ia.647 | F | Cl | CN | CH(CH₂CH₃)CONHCH₃ |
| Ia.648 | Cl | Cl | CN | CH(CH₂CH₃)CONHCH₃ |
| Ia.649 | H | Cl | Cl | CH₂CON(CH₃)₂ |
| Ia.650 | F | Cl | Cl | CH₂CON(CH₃)₂ |
| Ia.651 | Cl | Cl | Cl | CH₂CON(CH₃)₂ |
| Ia.652 | H | Cl | Br | CH₂CON(CH₃)₂ |
| Ia.653 | F | Cl | Br | CH₂CON(CH₃)₂ |
| Ia.654 | Cl | Cl | Br | CH₂CON(CH₃)₂ |
| Ia.655 | H | Cl | F | CH₂CON(CH₃)₂ |
| Ia.656 | F | Cl | F | CH₂CON(CH₃)₂ |
| Ia.657 | Cl | Cl | F | CH₂CON(CH₃)₂ |
| Ia.658 | H | Cl | I | CH₂CON(CH₃)₂ |
| Ia.659 | F | Cl | I | CH₂CON(CH₃)₂ |
| Ia.660 | Cl | Cl | I | CH₂CON(CH₃)₂ |
| Ia.661 | H | Cl | NO₂ | CH₂CON(CH₃)₂ |
| Ia.662 | F | Cl | NO₂ | CH₂CON(CH₃)₂ |
| Ia.663 | Cl | Cl | NO₂ | CH₂CON(CH₃)₂ |
| Ia.664 | H | Cl | CN | CH₂CON(CH₃)₂ |
| Ia.665 | F | Cl | CN | CH₂CON(CH₃)₂ |
| Ia.666 | Cl | Cl | CN | CH₂CON(CH₃)₂ |
| Ia.667 | H | Cl | Cl | CH₂CHN=OCH₃ |
| Ia.668 | F | Cl | Cl | CH₂CHN=OCH₃ |
| Ia.669 | Cl | Cl | Cl | CH₂CHN=OCH₃ |
| Ia.670 | H | Cl | Br | CH₂CHN=OCH₃ |
| Ia.671 | F | Cl | Br | CH₂CHN=OCH₃ |
| Ia.672 | Cl | Cl | Br | CH₂CHN=OCH₃ |
| Ia.673 | H | Cl | F | CH₂CHN=OCH₃ |
| Ia.674 | F | Cl | F | CH₂CHN=OCH₃ |
| Ia.675 | Cl | Cl | F | CH₂CHN=OCH₃ |
| Ia.676 | H | Cl | I | CH₂CHN=OCH₃ |
| Ia.677 | F | Cl | I | CH₂CHN=OCH₃ |
| Ia.678 | Cl | Cl | I | CH₂CHN=OCH₃ |
| Ia.679 | H | Cl | NO₂ | CH₂CHN=OCH₃ |
| Ia.680 | F | Cl | NO₂ | CH₂CHN=OCH₃ |
| Ia.681 | Cl | Cl | NO₂ | CH₂CHN=OCH₃ |
| Ia.682 | H | Cl | CN | CH₂CHN=OCH₃ |
| Ia.683 | F | Cl | CN | CH₂CHN=OCH₃ |
| Ia.684 | Cl | Cl | CN | CH₂CHN=OCH₃ |
| Ia.685 | H | Cl | Cl | CH₂CHN=OCH₂CH₃ |
| Ia.686 | F | Cl | Cl | CH₂CHN=OCH₂CH₃ |
| Ia.687 | Cl | Cl | Cl | CH₂CHN=OCH₂CH₃ |
| Ia.688 | H | Cl | Br | CH₂CHN=OCH₂CH₃ |
| Ia.689 | F | Cl | Br | CH₂CHN=OCH₂CH₃ |
| Ia.690 | Cl | Cl | Br | CH₂CHN=OCH₂CH₃ |
| Ia.691 | H | Cl | F | CH₂CHN=OCH₂CH₃ |
| Ia.692 | F | Cl | F | CH₂CHN=OCH₂CH₃ |
| Ia.693 | Cl | Cl | F | CH₂CHN=OCH₂CH₃ |
| Ia.694 | H | Cl | I | CH₂CHN=OCH₂CH₃ |
| Ia.695 | F | Cl | I | CH₂CHN=OCH₂CH₃ |
| Ia.696 | Cl | Cl | I | CH₂CHN=OCH₂CH₃ |
| Ia.697 | H | Cl | CN | CH₂CHN=OCH₂CH₃ |
| Ia.698 | F | Cl | CN | CH₂CHN=OCH₂CH₃ |
| Ia.699 | Cl | Cl | CN | CH₂CHN=OCH₂CH₃ |
| Ia.700 | H | Cl | NO₂ | CH₂CHN=OCH₂CH₃ |
| Ia.701 | F | Cl | NO₂ | CH₂CHN=OCH₂CH₃ |
| Ia.702 | Cl | Cl | NO₂ | CH₂CHN=OCH₂CH₃ |
| Ia.703 | H | Cl | Cl | CH₂CH(OCH₃)₂ |
| Ia.704 | F | Cl | Cl | CH₂CH(OCH₃)₂ |
| Ia.705 | Cl | Cl | Cl | CH₂CH(OCH₃)₂ |
| Ia.706 | H | Cl | Br | CH₂CH(OCH₃)₂ |
| Ia.707 | F | Cl | Br | CH₂CH(OCH₃)₂ |
| Ia.708 | Cl | Cl | Br | CH₂CH(OCH₃)₂ |
| Ia.709 | H | Cl | F | CH₂CH(OCH₃)₂ |
| Ia.710 | F | Cl | F | CH₂CH(OCH₃)₂ |
| Ia.711 | Cl | Cl | F | CH₂CH(OCH₃)₂ |
| Ia.712 | H | Cl | I | CH₂CH(OCH₃)₂ |
| Ia.713 | F | Cl | I | CH₂CH(OCH₃)₂ |
| Ia.714 | Cl | Cl | I | CH₂CH(OCH₃)₂ |
| Ia.715 | H | Cl | CN | CH₂CH(OCH₃)₂ |
| Ia.716 | F | Cl | CN | CH₂CH(OCH₃)₂ |
| Ia.717 | Cl | Cl | CN | CH₂CH(OCH₃)₂ |
| Ia.718 | H | Cl | NO₂ | CH₂CH(OCH₃)₂ |
| Ia.719 | F | Cl | NO₂ | CH₂CH(OCH₃)₂ |
| Ia.720 | Cl | Cl | NO₂ | CH₂CH(OCH₃)₂ |
| Ia.721 | H | Cl | Cl | CH₂CH(OCH₂CH₃)₂ |
| Ia.722 | F | Cl | Cl | CH₂CH(OCH₂CH₃)₂ |
| Ia.723 | Cl | Cl | Cl | CH₂CH(OCH₂CH₃)₂ |
| Ia.724 | H | Cl | Br | CH₂CH(OCH₂CH₃)₂ |
| Ia.725 | F | Cl | Br | CH₂CH(OCH₂CH₃)₂ |
| Ia.726 | Cl | Cl | Br | CH₂CH(OCH₂CH₃)₂ |
| Ia.727 | H | Cl | F | CH₂CH(OCH₂CH₃)₂ |
| Ia.728 | F | Cl | F | CH₂CH(OCH₂CH₃)₂ |
| Ia.729 | Cl | Cl | F | CH₂CH(OCH₂CH₃)₂ |
| Ia.730 | H | Cl | I | CH₂CH(OCH₂CH₃)₂ |
| Ia.731 | F | Cl | I | CH₂CH(OCH₂CH₃)₂ |
| Ia.732 | Cl | Cl | I | CH₂CH(OCH₂CH₃)₂ |
| Ia.733 | H | Cl | NO₂ | CH₂CH(OCH₂CH₃)₂ |
| Ia.734 | F | Cl | NO₂ | CH₂CH(OCH₂CH₃)₂ |

TABLE 2-continued

| No. | R³ | R⁴ | R⁵ | R⁷ |
|---|---|---|---|---|
| Ia.735 | Cl | Cl | NO₂ | CH₂CH(OCH₂CH₃)₂ |
| Ia.736 | H | Cl | CN | CH₂CH(OCH₂CH₃)₂ |
| Ia.737 | F | Cl | CN | CH₂CH(OCH₂CH₃)₂ |
| Ia.738 | Cl | Cl | CN | CH₂CH(OCH₂CH₃)₂ |
| Ia.739 | H | Cl | Cl | CH₂C(Cl)=CH₂ |
| Ia.740 | F | Cl | Cl | CH₂C(Cl)=CH₂ |
| Ia.741 | Cl | Cl | Cl | CH₂C(Cl)=CH₂ |
| Ia.742 | H | Cl | Br | CH₂C(Cl)=CH₂ |
| Ia.743 | F | Cl | Br | CH₂C(Cl)=CH₂ |
| Ia.744 | Cl | Cl | Br | CH₂C(Cl)=CH₂ |
| Ia.745 | H | Cl | F | CH₂C(Cl)=CH₂ |
| Ia.746 | F | Cl | F | CH₂C(Cl)=CH₂ |
| Ia.747 | Cl | Cl | F | CH₂C(Cl)=CH₂ |
| Ia.748 | H | Cl | I | CH₂C(Cl)=CH₂ |
| Ia.749 | F | Cl | I | CH₂C(Cl)=CH₂ |
| Ia.750 | Cl | Cl | I | CH₂C(Cl)=CH₂ |
| Ia.751 | H | Cl | NO₂ | CH₂C(Cl)=CH₂ |
| Ia.752 | F | Cl | NO₂ | CH₂C(Cl)=CH₂ |
| Ia.753 | Cl | Cl | NO₂ | CH₂C(Cl)=CH₂ |
| Ia.754 | H | Cl | CN | CH₂C(Cl)=CH₂ |
| Ia.755 | F | Cl | CN | CH₂C(Cl)=CH₂ |
| Ia.756 | Cl | Cl | CN | CH₂C(Cl)=CH₂ |
| Ia.757 | H | Cl | Cl | Phenyl |
| Ia.758 | F | Cl | Cl | Phenyl |
| Ia.759 | Cl | Cl | Cl | Phenyl |
| Ia.760 | H | Cl | Br | Phenyl |
| Ia.761 | F | Cl | Br | Phenyl |
| Ia.762 | Cl | Cl | Br | Phenyl |
| Ia.763 | H | Cl | F | Phenyl |
| Ia.764 | F | Cl | F | Phenyl |
| Ia.765 | Cl | Cl | F | Phenyl |
| Ia.766 | H | Cl | I | Phenyl |
| Ia.767 | F | Cl | I | Phenyl |
| Ia.768 | Cl | Cl | I | Phenyl |
| Ia.769 | H | Cl | NO₂ | Phenyl |
| Ia.770 | F | Cl | NO₂ | Phenyl |
| Ia.771 | Cl | Cl | NO₂ | Phenyl |
| Ia.772 | H | Cl | CN | Phenyl |
| Ia.773 | F | Cl | CN | Phenyl |
| Ia.774 | Cl | Cl | CN | Phenyl |
| Ia.775 | H | Cl | Cl | 2-F-phenyl |
| Ia.776 | F | Cl | Cl | 2-F-phenyl |
| Ia.777 | Cl | Cl | Cl | 2-F-phenyl |
| Ia.778 | H | Cl | Br | 2-F-phenyl |
| Ia.779 | F | Cl | Br | 2-F-phenyl |
| Ia.780 | Cl | Cl | Br | 2-F-phenyl |
| Ia.781 | H | Cl | F | 2-F-phenyl |
| Ia.782 | F | Cl | F | 2-F-phenyl |
| Ia.783 | Cl | Cl | F | 2-F-phenyl |
| Ia.784 | H | Cl | I | 2-F-phenyl |
| Ia.785 | F | Cl | I | 2-F-phenyl |
| Ia.786 | Cl | Cl | I | 2-F-phenyl |
| Ia.787 | H | Cl | NO₂ | 2-F-phenyl |
| Ia.788 | F | Cl | NO₂ | 2-F-phenyl |
| Ia.789 | Cl | Cl | NO₂ | 2-F-phenyl |
| Ia.790 | H | Cl | CN | 2-F-phenyl |
| Ia.791 | F | Cl | CN | 2-F-phenyl |
| Ia.792 | Cl | Cl | CN | 2-F-phenyl |
| Ia.793 | H | Cl | Cl | 3-F-phenyl |
| Ia.794 | F | Cl | Cl | 3-F-phenyl |
| Ia.795 | Cl | Cl | Cl | 3-F-phenyl |
| Ia.796 | H | Cl | Br | 3-F-phenyl |
| Ia.797 | F | Cl | Br | 3-F-phenyl |
| Ia.798 | Cl | Cl | Br | 3-F-phenyl |
| Ia.799 | H | Cl | F | 3-F-phenyl |
| Ia.800 | F | Cl | F | 3-F-phenyl |
| Ia.801 | Cl | Cl | F | 3-F-phenyl |
| Ia.802 | H | Cl | I | 3-F-phenyl |
| Ia.803 | F | Cl | I | 3-F-phenyl |
| Ia.804 | Cl | Cl | I | 3-F-phenyl |
| Ia.805 | H | Cl | NO₂ | 3-F-phenyl |
| Ia.806 | F | Cl | NO₂ | 3-F-phenyl |
| Ia.807 | Cl | Cl | NO₂ | 3-F-phenyl |
| Ia.808 | H | Cl | CN | 3-F-phenyl |
| Ia.809 | F | Cl | CN | 3-F-phenyl |
| Ia.810 | Cl | Cl | CN | 3-F-phenyl |
| Ia.811 | H | Cl | Cl | 4-F-phenyl |
| Ia.812 | F | Cl | Cl | 4-F-phenyl |
| Ia.813 | Cl | Cl | Cl | 4-F-phenyl |
| Ia.814 | H | Cl | Br | 4-F-phenyl |
| Ia.815 | F | Cl | Br | 4-F-phenyl |
| Ia.816 | Cl | Cl | Br | 4-F-phenyl |
| Ia.817 | H | Cl | F | 4-F-phenyl |
| Ia.818 | F | Cl | F | 4-F-phenyl |
| Ia.819 | Cl | Cl | F | 4-F-phenyl |
| Ia.820 | H | Cl | I | 4-F-phenyl |
| Ia.821 | F | Cl | I | 4-F-phenyl |
| Ia.822 | Cl | Cl | I | 4-F-phenyl |
| Ia.823 | H | Cl | NO₂ | 4-F-phenyl |
| Ia.824 | F | Cl | NO₂ | 4-F-phenyl |
| Ia.825 | Cl | Cl | NO₂ | 4-F-phenyl |
| Ia.826 | H | Cl | CN | 4-F-phenyl |
| Ia.827 | F | Cl | CN | 4-F-phenyl |
| Ia.828 | Cl | Cl | CN | 4-F-phenyl |
| Ia.829 | H | Cl | Cl | 2-Cl-phenyl |
| Ia.830 | F | Cl | Cl | 2-Cl-phenyl |
| Ia.831 | Cl | Cl | Cl | 2-Cl-phenyl |
| Ia.832 | H | Cl | Br | 2-Cl-phenyl |
| Ia.833 | F | Cl | Br | 2-Cl-phenyl |
| Ia.834 | Cl | Cl | Br | 2-Cl-phenyl |
| Ia.835 | H | Cl | F | 2-Cl-phenyl |
| Ia.836 | F | Cl | F | 2-Cl-phenyl |
| Ia.837 | Cl | Cl | F | 2-Cl-phenyl |
| Ia.838 | H | Cl | I | 2-Cl-phenyl |
| Ia.839 | F | Cl | I | 2-Cl-phenyl |
| Ia.840 | Cl | Cl | I | 2-Cl-phenyl |
| Ia.841 | H | Cl | CN | 2-Cl-phenyl |
| Ia.842 | F | Cl | CN | 2-Cl-phenyl |
| Ia.843 | Cl | Cl | CN | 2-Cl-phenyl |
| Ia.844 | H | Cl | NO₂ | 2-Cl-phenyl |
| Ia.845 | F | Cl | NO₂ | 2-Cl-phenyl |
| Ia.846 | Cl | Cl | NO₂ | 2-Cl-phenyl |
| Ia.847 | H | Cl | Cl | 3-Cl-phenyl |
| Ia.848 | F | Cl | Cl | 3-Cl-phenyl |
| Ia.849 | Cl | Cl | Cl | 3-Cl-phenyl |
| Ia.850 | H | Cl | Br | 3-Cl-phenyl |
| Ia.851 | F | Cl | Br | 3-Cl-phenyl |
| Ia.852 | Cl | Cl | Br | 3-Cl-phenyl |
| Ia.853 | H | Cl | F | 3-Cl-phenyl |
| Ia.854 | F | Cl | F | 3-Cl-phenyl |
| Ia.855 | Cl | Cl | F | 3-Cl-phenyl |
| Ia.856 | H | Cl | I | 3-Cl-phenyl |
| Ia.857 | F | Cl | I | 3-Cl-phenyl |
| Ia.858 | Cl | Cl | I | 3-Cl-phenyl |
| Ia.859 | H | Cl | NO₂ | 3-Cl-phenyl |
| Ia.860 | F | Cl | NO₂ | 3-Cl-phenyl |
| Ia.861 | Cl | Cl | NO₂ | 3-Cl-phenyl |
| Ia.862 | H | Cl | CN | 3-Cl-phenyl |
| Ia.863 | F | Cl | CN | 3-Cl-phenyl |
| Ia.864 | Cl | Cl | CN | 3-Cl-phenyl |

TABLE 2-continued

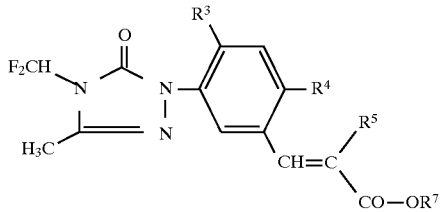

Ia

| No. | R³ | R⁴ | R⁵ | R⁷ |
|---|---|---|---|---|
| Ia.865 | H | Cl | Cl | 4-Cl-phenyl |
| Ia.866 | F | Cl | Cl | 4-Cl-phenyl |
| Ia.867 | Cl | Cl | Cl | 4-Cl-phenyl |
| Ia.868 | H | Cl | Br | 4-Cl-phenyl |
| Ia.869 | F | Cl | Br | 4-Cl-phenyl |
| Ia.870 | Cl | Cl | Br | 4-Cl-phenyl |
| Ia.871 | H | Cl | F | 4-Cl-phenyl |
| Ia.872 | F | Cl | F | 4-Cl-phenyl |
| Ia.873 | Cl | Cl | F | 4-Cl-phenyl |
| Ia.874 | H | Cl | I | 4-Cl-phenyl |
| Ia.875 | F | Cl | I | 4-Cl-phenyl |
| Ia.876 | Cl | Cl | I | 4-Cl-phenyl |
| Ia.877 | H | Cl | NO₂ | 4-Cl-phenyl |
| Ia.878 | F | Cl | NO₂ | 4-Cl-phenyl |
| Ia.879 | Cl | Cl | NO₂ | 4-Cl-phenyl |
| Ia.880 | H | Cl | CN | 4-Cl-phenyl |
| Ia.881 | F | Cl | CN | 4-Cl-phenyl |
| Ia.882 | Cl | Cl | CN | 4-Cl-phenyl |
| Ia.883 | H | Cl | Cl | 2-CO₂CH₃-phenyl |
| Ia.884 | F | Cl | Cl | 2-CO₂CH₃-phenyl |
| Ia.885 | Cl | Cl | Cl | 2-CO₂CH₃-phenyl |
| Ia.886 | H | Cl | Br | 2-CO₂CH₃-phenyl |
| Ia.887 | F | Cl | Br | 2-CO₂CH₃-phenyl |
| Ia.888 | Cl | Cl | Br | 2-CO₂CH₃-phenyl |
| Ia.889 | H | Cl | F | 2-CO₂CH₃-phenyl |
| Ia.890 | F | Cl | F | 2-CO₂CH₃-phenyl |
| Ia.891 | Cl | Cl | F | 2-CO₂CH₃-phenyl |
| Ia.892 | H | Cl | I | 2-CO₂CH₃-phenyl |
| Ia.893 | F | Cl | I | 2-CO₂CH₃-phenyl |
| Ia.894 | Cl | Cl | I | 2-CO₂CH₃-phenyl |
| Ia.895 | H | Cl | NO₂ | 2-CO₂CH₃-phenyl |
| Ia.896 | F | Cl | NO₂ | 2-CO₂CH₃-phenyl |
| Ia.897 | Cl | Cl | NO₂ | 2-CO₂CH₃-phenyl |
| Ia.898 | H | Cl | CN | 2-CO₂CH₃-phenyl |
| Ia.899 | F | Cl | CN | 2-CO₂CH₃-phenyl |
| Ia.900 | Cl | Cl | CN | 2-CO₂CH₃-phenyl |
| Ia.901 | H | Cl | Cl | 3-CO₂CH₃-phenyl |
| Ia.902 | F | Cl | Cl | 3-CO₂CH₃-phenyl |
| Ia.903 | Cl | Cl | Cl | 3-CO₂CH₃-phenyl |
| Ia.904 | H | Cl | Br | 3-CO₂CH₃-phenyl |
| Ia.905 | F | Cl | Br | 3-CO₂CH₃-phenyl |
| Ia.906 | Cl | Cl | Br | 3-CO₂CH₃-phenyl |
| Ia.907 | H | Cl | F | 3-CO₂CH₃-phenyl |
| Ia.908 | F | Cl | F | 3-CO₂CH₃-phenyl |
| Ia.909 | Cl | Cl | F | 3-CO₂CH₃-phenyl |
| Ia.910 | H | Cl | I | 3-CO₂CH₃-phenyl |
| Ia.911 | F | Cl | I | 3-CO₂CH₃-phenyl |
| Ia.912 | Cl | Cl | I | 3-CO₂CH₃-phenyl |
| Ia.913 | H | Cl | NO₂ | 3-CO₂CH₃-phenyl |
| Ia.914 | F | Cl | NO₂ | 3-CO₂CH₃-phenyl |
| Ia.915 | Cl | Cl | NO₂ | 3-CO₂CH₃-phenyl |
| Ia.916 | H | Cl | CN | 3-CO₂CH₃-phenyl |
| Ia.917 | F | Cl | CN | 3-CO₂CH₃-phenyl |
| Ia.918 | Cl | Cl | CN | 3-CO₂CH₃-phenyl |
| Ia.919 | H | Cl | Cl | 4-CO₂CH₃-phenyl |
| Ia.920 | F | Cl | Cl | 4-CO₂CH₃-phenyl |
| Ia.921 | Cl | Cl | Cl | 4-CO₂CH₃-phenyl |
| Ia.922 | H | Cl | Br | 4-CO₂CH₃-phenyl |
| Ia.923 | F | Cl | Br | 4-CO₂CH₃-phenyl |
| Ia.924 | Cl | Cl | Br | 4-CO₂CH₃-phenyl |
| Ia.925 | H | Cl | F | 4-CO₂CH₃-phenyl |
| Ia.926 | F | Cl | F | 4-CO₂CH₃-phenyl |
| Ia.927 | Cl | Cl | F | 4-CO₂CH₃-phenyl |
| Ia.928 | H | Cl | I | 4-CO₂CH₃-phenyl |
| Ia.929 | F | Cl | I | 4-CO₂CH₃-phenyl |

TABLE 2-continued

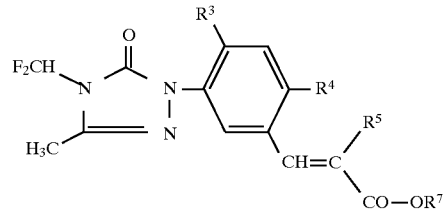

Ia

| No. | R³ | R⁴ | R⁵ | R⁷ |
|---|---|---|---|---|
| Ia.930 | Cl | Cl | I | 4-CO₂CH₃-phenyl |
| Ia.931 | H | Cl | NO₂ | 4-CO₂CH₃-phenyl |
| Ia.932 | F | Cl | NO₂ | 4-CO₂CH₃-phenyl |
| Ia.933 | Cl | Cl | NO₂ | 4-CO₂CH₃-phenyl |
| Ia.934 | H | Cl | CN | 4-CO₂CH₃-phenyl |
| Ia.935 | F | Cl | CN | 4-CO₂CH₃-phenyl |
| Ia.936 | Cl | Cl | CN | 4-CO₂CH₃-phenyl |
| Ia.937 | H | Cl | Cl | CH₂-phenyl |
| Ia.938 | F | Cl | Cl | CH₂-phenyl |
| Ia.939 | Cl | Cl | Cl | CH₂-phenyl |
| Ia.940 | H | Cl | Br | CH₂-phenyl |
| Ia.941 | F | Cl | Br | CH₂-phenyl |
| Ia.942 | Cl | Cl | Br | CH₂-phenyl |
| Ia.943 | H | Cl | F | CH₂-phenyl |
| Ia.944 | F | Cl | F | CH₂-phenyl |
| Ia.945 | Cl | Cl | F | CH₂-phenyl |
| Ia.946 | H | Cl | I | CH₂-phenyl |
| Ia.947 | F | Cl | I | CH₂-phenyl |
| Ia.948 | Cl | Cl | I | CH₂-phenyl |
| Ia.949 | H | Cl | NO₂ | CH₂-phenyl |
| Ia.950 | F | Cl | NO₂ | CH₂-phenyl |
| Ia.951 | Cl | Cl | NO₂ | CH₂-phenyl |
| Ia.952 | H | Cl | CN | CH₂-phenyl |
| Ia.953 | F | Cl | CN | CH₂-phenyl |
| Ia.954 | Cl | Cl | CN | CH₂-phenyl |

Furthermore, the following substituted triazolinones I are particularly preferred:

the compounds Ib.001 to Ib.954, which differ from the compounds Ia.001 to Ia.954 in that X is sulfur:

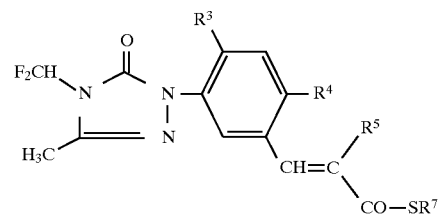

Ib the compounds Ic.001 to Ic.954, which differ from the compounds Ia.001 to Ia.954 in that X is amino:

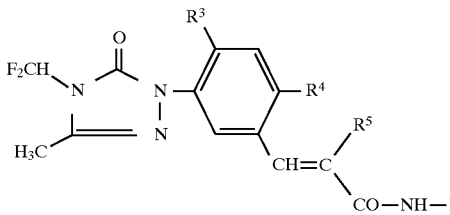

Ic the compounds Id.001 to Id.954, which differ from the compounds Ia.001 to Ia.954 in that X is aminomethyl:

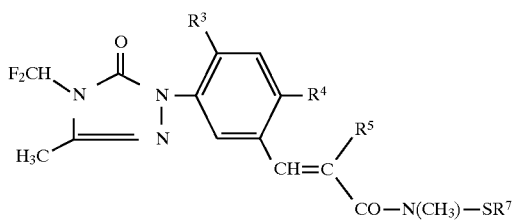

The substituted triazolinones of the formula I are obtainable by various methods, for example by one of the following processes:

Process A:

Diazotization of substituted anilines II and reaction of the resulting diazonium salts with alkynes III in a manner known per se by the Meerwein method (cf. for example N. I. Ganushchak et al., Zh. Organ. Ximii. (16) HO12 (1980), 2578–2581):

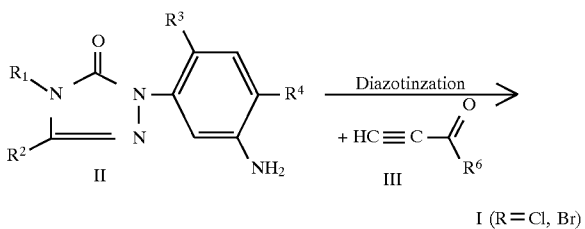

In this type of reaction, the substituted aniline II is first converted into a diazonium salt. This then reacts with the alkyn III in the presence of a copper salt.

The phenyldiazonium salt is advantageously prepared in a manner known per se by reacting the substituted aniline II in an aqueous acid solution, for example in aqueous hydrochloric acid, hydrobromic acid or sulfuric acid, with a nitrite, such as sodium nitrite or potassium nitrite, and is reacted with the alkyn III in an inert solvent in the presence of a copper halide, such as copper(I) chloride, copper(I) bromide, copper(II) chloride or copper(II) bromide.

Examples of suitable inert solvents are water, acetonitrile, ketones, such as acetone, diethyl ketone and methyl ethyl ketone, ethers, such as dioxane and tetrahydrofuran, and alcohols, such as methanol and ethanol.

A further possibility for the preparation of the phenyldiazonium salt is to react the aniline II in an anhydrous system, for example in glacial acetic acid which contains hydrogen chloride, or in dioxane, absolute ethanol, tetrahydrofuran, acetonitrile or acetone, with an ester of nitrous acid, such as tert-butyl nitrite or isopentyl nitrite. In this case, the diazotization can take place in the presence of the alkyn III and of the copper halide.

The reaction temperature is usually from −30 to 80° C.

Usually, the components of the diazotization reaction are used in a roughly stoichiometric ratio, but an excess of one of the components may also be advantageous, for example in order to achieve as complete a conversion of the other component as possible.

The alkyn III can be used in equimolar amounts, in excess or in less than the stoichiometric amount, based on the phenyldiazonium salt. In general, a large excess, based on the phenyldiazonium salt, of alkyn III has proven particularly advantageous. The copper halide is usually used in a stoichiometric ratio, but an excess or less than the stoichiometric amount is also possible.

Process B:

Reaction of a substituted benzaldehyde IV with an ylide of the formula V in a manner known per se (cf. for example R. S. Mali and V. J. Yadav, Synthesis 10 (1984), 862):

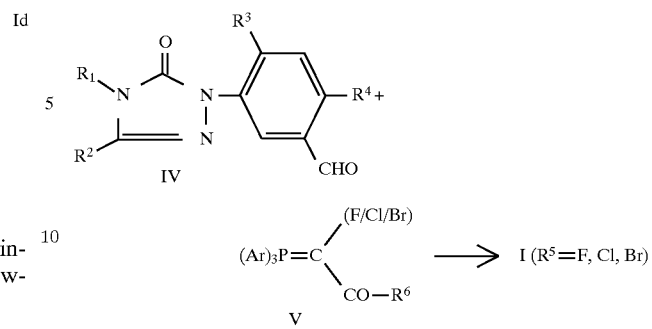

Ar is an aromatic radical which, if desired, may be substituted, preferably phenyl.

Examples of suitable solvents are aromatic hydrocarbons, such as benzene and toluene, ethers, such as diethyl ether, tetrahydrofuran and dioxane, dipolar aprotic solvents such as dimethyl sulfoxide and dimethylformamide and protic solvents, such as methanol and ethanol. Mixtures of the stated solvents are also suitable.

The reaction is usually carried out at from 0° C. to the boiling point of the particular reaction mixture.

The substituted benzaldehyde and ylide are usually used in roughly stoichiometric amounts, but it is also possible to use one of the components in excess.

Process C:

Reaction of a substituted benzaldehyde IV with a CH-acidic compound $NO_2$—$CH_2$—$COR^6$ or NC—$CH_2$—$COR^6$ in a manner known per se (cf. for example J. March, "Advanced Organic Chemistry", page 835 et seq.):

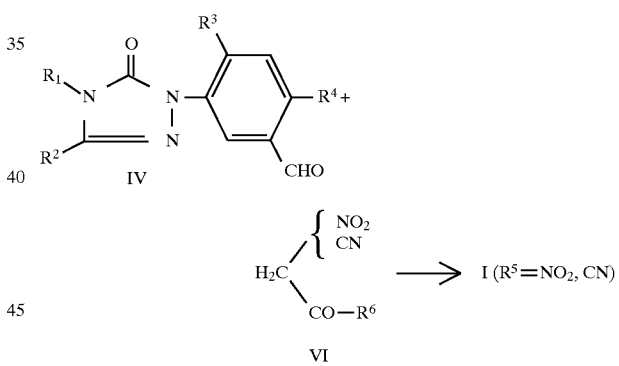

Depending on the particular substituents and on the reaction conditions, it may be advantageous to carry out the reaction in the presence of a catalytic amount or in a roughly equivalent amount, based on VI, of a base or in the presence of an acid.

Examples of suitable bases are metal alcoholates, such as sodium methylate, sodium ethylate and potassium tert-butylate, aromatic or-aliphatic nitrogen bases, such as pyridine, piperidine, triethylamine, ammonium acetate and β-alanine, and metal hydrides such as sodium hydride and potassium hydride.

Particularly useful acids are acetic acid and propionic acid.

The reaction is carried out either in the absence of a solvent or in an excess of base or acid or in an inert solvent or diluent. For example, alcohols, such as methanol and ethanol, or ethers, such as diethyl ether and methyl tert-butyl ether, are suitable solvents, depending on the reaction conditions.

The reaction is carried out in general at from 0° C. to the boiling point of the reaction mixture.

Usually, the starting compounds IV and VI are used in roughly equivalent amounts, but one of the components may also be used in excess.

Process D:

Reaction of an activated carboxylic acid VII with a nucleophile VIII in a manner known per se (cf. for example J. March, "Advanced Organic Chemistry", page 348 et seq.):

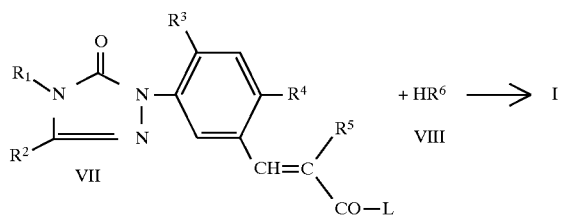

L is a conventional leaving group, such as chlorine, bromine or 1-imidazolyl.

If L is chlorine or bromine, the presence of a base, such as triethylamine or pyridine, may be advisable.

Examples of suitable solvents are halohydrocarbons, such as methylene chloride and 1,2-dichloroethane, aromatic hydrocarbons and halohydrocarbons, such as benzene, toluene and chlorobenzene, ethers, such as diethyl ether, tetrahydrofuran, methyl tert-butyl ether and dioxane, dipolar aprotic solvents, such as dimethyl sulfoxide and dimethylformamide, and mixtures of such solvents.

The reaction is carried out in general at from −20° C. to the boiling point of the reaction mixture.

Usually, the starting compounds are used in roughly stoichiometric amounts, unless it is advisable to use one of the components in excess.

The activated carboxylic acids VII in which L is chlorine or bromine are in turn obtainable in a manner known per se by reacting the corresponding carboxylic acids with a halogenating agent, for example with thionyl chloride, thionyl bromide, sulfuryl chloride, sulfuryl bromide, an organic sulfonyl chloride, such as tosyl chloride, phosphorus trichloride, phosphorus tribromide, phosphorus pentachloride, phosphorus pentabromide or phosphoryl bromide, or with a binary halogenating system, such as tetrachloromethane/triphenylphosphine or tetrabromomethane/triphenylphosphine.

The halogenation can be carried out without a solvent or in an inert solvent. Depending on the halogenating agent, suitable solvents are in general, for example, halohydrocarbons, such as methylene chloride, chloroform and 1,2-dichloroethane, aromatic hydrocarbons and halohydreocarbons, such as benzene, toluene and chlorobenzene, dipolar aprotic solvents, such as acetonitrile, and carbon disulfide and ethers, such as diethyl ether, methyl tert-butyl ether and tetrahydrofuran. Mixtures of these solvents are also suitable.

The halogenation may be carried out at from −30° C. to the boiling point of the reaction mixture.

Depending on the halogenating agent, the acid to be halogenated is advantageously used in a stoichiometric amount or in less than the stoichiometric amount.

In a variant of the process, the activated carboxylic acid VII is prepared in situ, particularly if L is 1-imidazolyl or if the reaction is carried out under Mitsunobu conditions (cf. O. Mitsunobu, Synthesis 1981, 1).

The carboxylic acid to be activated is obtainable by one of the processes (A)–(C) or by hydrolysis of the corresponding esters of the formula I (where $R^6$ is —$OR^7$), which in turn can be prepared by process (A), (B) or (C).

Unless stated otherwise, all processes described above are advantageously carried out at atmospheric pressure or under the autogenous pressure of the particular reaction mixture.

The reaction mixtures are worked up, as a rule, by methods known per se, for example by removing the solvent, partitioning the residue in a mixture of water and a suitable organic solvent and working up the organic phase to obtain the product.

The substituted triazolinones of the formula I may contain one or more centers of chirality and, if so, are usually obtained as mixtures of enantiomers or of diastereomers. The mixtures can, if desired, be resolved into the substantially pure isomers by conventional methods, for example by means of crystallization or chromatography over an optically active adsorbate. Pure optically active isomers can also be prepared, for example, from corresponding optically active starting materials.

In particular, those compounds I in which $R^1$ is hydrogen and/or $R^6$ is hydroxyl, mercapto, —$NHR^8$ or —$N(R^8)$—OH can be converted in a manner known per se into their salts, preferably into their alkali metal salts.

Salts of the substituted triazolinones I whose metal ion is not an alkali metal ion can be prepared by double decomposition of the corresponding alkali metal salt in a conventional manner, as can ammonium and phosphonium salts by means of ammonia or phosphonium, sulfonium or sulfoxonium hydroxides.

The compounds I and their agriculturally useful salts are suitable, both in the form of isomer mixtures and in the form of the pure isomers, as herbicides. They can control weeds and grass weeds very well in crops such as wheat, rice, corn, soybean and cotton, without significantly damaging the crops. This effect occurs in particular at low application rates.

Depending on the particular application method, the compounds I or the herbicides containing them can also be used in a further number of crops for eliminating undesirable plants. For example, the following crops are suitable:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum(N. rustica), Olea europaea, Oryza sativa , Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays.*

In addition, the compounds I can be used in crops which have been made substantially resistant to the action of I by breeding and/or by genetic engineering methods.

Furthermore, the substituted triazolinones I are suitable for the desiccation and/or defoliation of plants.

As desiccants, they are suitable in particular for drying out the above-ground parts of crops such as potato, rape, sunflower and soybean. This permits complete mechanical harvesting of these important crops.

It is also of commercial interest to facilitation harvesting, this being achieved by the concentrated dropping or a reduction in the adhesion to the tree in the case of citrus fruits, olives or other species and varieties of pomes, drupes and indehiscent fruit. The same mechanism, ie. promotion of the formation of abscission tissue between fruit or leaf part and shoot part of the plants, is also important for readily controllable defoliation of crops, in particular cotton.

Furthermore, shortening the time interval in which the individual cotton plants ripen leads to higher fiber quality after the harvest.

The compounds I and the herbicides containing them can be applied, for example, in the form of directly sprayable aqueous solutions, powders, suspensions, including concentrated aqueous, oily or other suspensions or dispersions, emulsions, oil dispersions, pastes, dusting agents, broadcasting agents or granules, by spraying, nebulizing, dusting, broadcasting or pouring. The application forms depend on the intended uses; they should in any case ensure a very fine distribution of the novel active ingredients.

Suitable inert assistants for the preparation of directly sprayable solutions, emulsions, pastes or oil dispersions are essentially mineral oil fractions having a medium to high boiling point, such as kerosene and diesel oil, and coaltar oils and oils of vegetable or animal origin, aliphatic, cyclic and aromatic hydrocarbons, for example paraffins, tetrahydronaphthalene, alkylated naphthalenes and their derivatives, alkylated benzenes and their derivatives, alcohols, such as methanol, ethanol, propanol, butanol and cyclohexanol, ketones, such as cyclohexanone, and strongly polar solvents, for example amines, such as N-methylpyrrolidone, and water.

Aqueous application forms can be prepared from emulsion concentrates, suspensions, pastes, wettable powders or water-dispersible granules by adding water. For the preparation of emulsions, pastes or oil dispersions, the substances, as such or dissolved in an oil or solvent, can be homogenized in water by means of wetting agents, adherents, dispersants or emulsifiers. However, it is also possible to prepare concentrates which consist of active ingredient, wetting agents, adherents, dispersants or emulsifiers and possibly solvents or oils and which are suitable for dilution with water.

Suitable surfactants are the alkali metal, alkaline earth metal and ammonium salts of aromatic sulfonic acids, for example ligninsulfonic, phenylsulfonic, naphthalene-sulfonic and dibutylnaphthalenesulfonic acid, and of fatty acids, alkylsulfonates and alkylarylsulfonates, alkylsulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, ligninsulfite waste liquors or methylcellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders or other solid carriers.

The concentrations of the active ingredients I in the ready-to-use compositions can be varied within wide ranges, for example from 0.01 to 95, particularly from 0.5 to 90, % by weight. The active ingredients are used in a purity of from 90 to 100%, preferably from 95 to 100% (according to the NMR spectrum).

The following formulation examples illustrate the preparation of such compositions:

I. 20 parts by weight of compound No. I.01 are dissolved in a mixture which consists of 80 parts by weight of alkylated benzene, 10 parts by weight of the adduct of from 8 to 10 mol of ethylene oxide with 1 mol of oleic acid N-monoethanoleamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

II. 20 parts by weight of compound I.02 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

II. 20 parts by weight of active ingredient No. I.03 are dissolved in a mixture which consists of 25 parts by weight of cyclohexanone, 65 parts by weight of a mineral oil fraction boiling within the range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. I.04 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

V. 3 parts by weight of active ingredient No. I.05 are mixed with 97 parts by weight of finely divided kaolin. A dusting agent which contains 3% by weight of the active ingredient is obtained in this manner.

VI. 20 parts by weight of weight of active ingredient I.02 are intimately mixed with 2 parts by weight of the calcium salt of dodecylbenzenesulfonic acid, 8 parts by weight of a fatty alcohol polyglycol ether, 2 parts by weight of the sodium salt of a phenol/urea/ formaldehyde condensate and 68 parts by weight of a paraffinic mineral oil. A stable oily dispersion is obtained.

The active ingredients I or the herbicides are applied by the preemergence or postemergence method. If the active ingredients are less well tolerated by certain crops, it is possible to use application methods in which the herbicides are sprayed with the aid of the sprays in such a way that the leaves of the sensitive crops are as far as possible not affected, while the active ingredients reach the leaves of undesirable plants growing underneath or the uncovered soil surface (post-directed, lay-by).

The application rates of active ingredient I are from 0.001 to 3.0, preferably from 0.01 to 1, kg/ha of active ingredient (a.s.), depending on the aim of control, the season, the target plants and the stage of growth.

In order to broaden the action spectrum and to achieve synergistic effects, the substituted triazolinones I can be mixed with many members of other groups of herbicidal or growth-regulating active ingredients and applied together with them. Examples of suitable components for the mixture are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry, for example, a carboxyl or carbimino group in the 2 position, quinolinecarboxylic acid derivatives, imidazolinones, sulfonamides, sulfonylureas, aryloxy- and heteroaryloxyphenoxypropionic acids and their salts, esters and amides and others.

It may also be useful to apply the compounds I, alone or in combination with other herbicides, also mixed with further crop protection agents, for example with pesticides or agents for controlling phytopathogenic fungi or bacteria. Also of interest is the miscibility with mineral salt solutions which are used for eliminating nutrient and trace element deficiencies. Nonphytotoxic oils and oil concentrates may also be added.

Preparation example

1-[4-Chloro-5-(2-chloro-2-ethoxycarbonylethen-1-yl)-2-fluorophenyl)]-4-difluoromethyl-4-methyltriazolin-5-one (I.02)

2.9 g 1-[5-amino-4-chloro-2-fluorophenyl)]-4-difluoromethyl-4-methyltriazolin-5-one in 20 ml of absolute acetonitrile were added dropwise to a suspension of 1.6 g of tert-butyl nitrite, 21.6 g of ethyl propiolate and 1.6 g of anhydrous copper(II) chloride in 400 ml of absolute acetonitrile. After stirring had been carried out for 12 hours at 20°–25° C., dilute aqueous hydrochloric acid was added to the reaction mixture. The product was then extracted with methyl tert-butyl ether. Combined organic phases were dried over sodium sulfate, after which the solvent was removed under reduced pressure. The residue was purified by chromatography over silica gel (eluent: 9:1 cyclohexane/methyl tert-butyl ether). Yield: 1.5 g (37%) [cis/trans mixture]

$^1$H-NMR (in CDCl$_3$; tetramethylsilane (TMS) as internal standard): δ [ppm]=1.14/1.40 (t, 3H); 2.45/2.48 (s, 3H); 4.16/4.34 (q, 2H); 7.03/7.07 (t, 1H); 7.31/7.40 (d, 1H); 7.38/8.06 (s, 1H); 7.48/8.18 (d, 1H).

Table 3 shows further triazolinones of the formula I, which were prepared or can be prepared in the same manner:

TABLE 3

I ($R^1$ = CHF$_2$; $R^2$ = CH$_3$)

| No. | $R^3$ | $R^4$ | $R^5$ | $R^6$ | M.p. [°C.]/$^1$H-NMR [δ in ppm] |
|---|---|---|---|---|---|
| I.01 | H | Cl | Cl | OC$_2$H$_5$ | 70–71 |
| I.02 | F | Cl | Cl | OC$_2$H$_5$ | 1.14/1.40 (s, 3H); 2.45/2.48 (s, 3H); 4.16/4.38 (q, 2H); 7.03/7.07 (t, 1H); 7.31/7.40 (d, 1H); 7.38/8.06 (s, 1H); 7.48/8.18 (d, 1H) |
| I.03 | F | Cl | Br | OCH$_3$ | 2.50/2.52 (s, 3H); 3.79/3.95 (s, 3H); 7.04/7.07 (t, 1H); 7.36/7.50 (d, 1H); 7.40/8.28 (s, 1H); 7.48/8.14 (d, 1H) |
| I.04 | H | Cl | Br | OCH$_3$ | 2.50 (s, 3H); 3.65/3.90 (s, 3H); 7.03 (t, 1H); 7.25–8.10 (m, 4H) |
| I.05 | F | Cl | Cl | OCH$_3$ | 100–101 |
| I.06 | F | Cl | Br | OC$_2$H$_5$ | 70–72 |
| I.07 | H | Cl | Cl | OCH(CH$_3$)$_2$ | 1.34 (d, 6H); 2.46 (s, 3H); 5.14 (sept, 1H); 7.04 (t, 1H); 7.40 (dd, 1H); 7.42 (d, 1H); 7.83 (s, 1H); 7.95 (d, 1H) |
| I.08 | H | Cl | Br | OC$_2$H$_5$ | 1.36 (t, 3H); 2.48/2.50 (s, 3H); 4.34 (m, 2H); 7.05/7.07 (t, 1H); 7.36–8.16 (m, 4H) |
| I.09 | H | Cl | Cl | OCH$_3$ | 62–63 (E isomer) |
| I.10 | H | Cl | Cl | OCH$_3$ | 125–126 (Z isomer) |

Use examples (herbicidal activity)

The herbicidal action of the substituted triazolinones I could be demonstrated by the following greenhouse experiments:

The culture vessels used were plastic flowerpots containing loamy sand with about 3.0% of humus as a substrate. The seeds of the test plants were sown separately according to species.

In the preemergence treatment, the active ingredients suspended and emulsified in water were applied directly after sowing by means of finely distributing nozzles. The vessels were lightly sprinkler-irrigated in order to promote germination and growth and then covered with transparent plastic covers until the plants had begun to grow. This covering produces uniform germination of the test plants, unless this was adversely affected by the active ingredients.

For the purpose of the postemergence treatment, the test plants were grown to a height of growth of from 3 to 15 cm, depending on the form of growth, before being treated with the active ingredients suspended or emulsified in water. For this purpose, the test plants were either directly sown and grown in the same vessels or they were first grown separately as seedlings and transplanted into the test vessels a few days before the treatment. The application rate for the postemergence treatment was 0.0156 or 0.0078 kg/ha of a.i. (active ingredient).

The plants were kept at 10°–25° C. or 20°–35° C., according to species. The test period extended over 2 to 4 weeks. During this time, the plants were tended and their reaction to the individual treatments was evaluated.

Evaluation was based on a scale of from 0 to 100. 100 means no emergence of the plants or complete destruction of at least the above-ground parts and 0 means no damage or normal course of growth.

The plants used in the greenhouse experiments consisted of the following species:

| Botanical name | Common name |
| --- | --- |
| Amaranthus retroflexus | redroot pigweed |
| Setaria faberii | giant foxtail |
| Setaria viridis | green foxtail |
| Veronica subspecies | speedwell |

At an application rate of 0.0078 or 0.0156 kg/ha of a.i., compound I.02 showed a very good action against the abovementioned plants in the postemergence method. In contrast, the compound

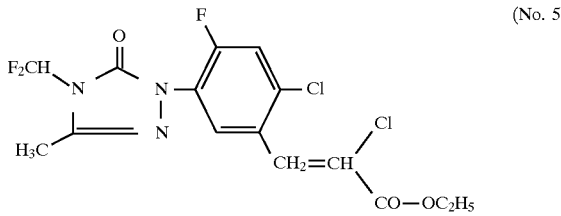

(No. 5)

disclosed in WO 90/02120 and likewise subjected to comparative test with regard to its herbicidal action was much less effective.

Use examples (desiccant/defoliant activity)

The test plants used were young, 4-leaf cotton plants (without cotyledons), which were grown under greenhouse conditions (relative humidity from 50 to 70%: day/night temperature 27°/20° C).

The foliage of the young cotton plants were sprayed to run off with aqueous preparations of the active ingredients (with the addition of 0.15% by weight, based on the spray liquor, of the fatty alcohol alkoxylate Plurafac LF 700). The amount of water applied was the equivalent of a 1000l/ha. After 13 days, the number of dropped leaves and the degree of defoliation were determined in %.

In the case of the untreated control plants, no shedding of leaves occurred.

We claim:

1. A triazolinone of the formula I

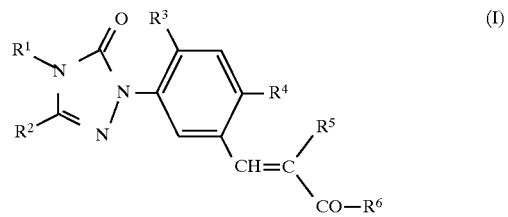

(I)

where $R^1$ is hydrogen, $C_1$–$C_6$-alkyl or $C_1$–$C_6$-haloalkyl;

$R^2$ is hydrogen, $C_1$–$C_6$-alkyl or $C_1$–$C_6$-haloalkyl;

$R^3$ is hydrogen or halogen;

$R^4$ is cyano, halogen, $C_1$–$C_6$-alkyl, $C_1$–$C_6$-haloalkyl, $C_1$–$C_6$-alkoxy or $C_1$–$C_1$–$C_6$-haloalkoxy;

$R^5$ is halogen;

$R^6$ is $OR^7$, $R^7$ is hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, cyano-$C_1$–$C_6$-alkyl, $C_1$–$C_6$-alkoxy-$C_1$–$C_6$-alkyl, $C_1$–$C_6$-alkylthio-$C_1$–$C_6$-alkyl, ($C_1$–$C_6$-alkoxy)carbonyl-$C_1$–$C_6$-alkyl, ($C_1$–$C_6$-alkylamino)carbonyl-$C_1$–$C_6$-alkyl, di-($C_1$–$C_6$-alkyl)aminocarbonyl-$C_1$–$C_6$-alkyl, $C_1$–$C_6$-alkoxyimino-$C_1$–$C_6$-alkyl, di-($C_1$–$C_6$-alkoxy)-$C_2$–$C_6$-alkyl, di-($C_1$–$C_6$-alkylthio)-$C_2$–$C_6$-alkyl, $C_3$–$C_6$-haloalkenyl, phenyl or benzyl, where each of the phenyl rings may carry one to three radicals selected from the group consisting of cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio and ($C_1$–$C_6$-alkoxy) carbonyl;

or an agriculturally useful salt of I.

2. The triazolinone of the formula I defined in claim 1, wherein $R^1$ is hydrogen, methyl or $C_1$–$C_6$-haloalkyl, and $R^2$ is hydrogen, $C_1$–$C_6$-alkyl or $C_1$–$C_4$-haloalkyl.

3. A herbicidal composition containing a herbicidal amount of a triazolinone of the formula I or an agriculturally useful salt of I, as defined in claim 1, and an inert liquid or solid carrier.

4. A plant desiccant or defoliant composition containing an amount, having a desiccant or defoliant action, of a triazolinone of the formula I or an agriculturally useful salt of I, as defined in claim 1, and an inert liquid or solid carrier.

5. A method for controlling undesirable plant growth, wherein a herbicidal amount of a triazolinone of the formula I or an agriculturally useful salt of I, as defined in claim 1, is allowed to act on plants or on their habitat or on seed.

6. A method for desiccation or defoliation of plants, wherein an amount, having desiccant or defoliant action, of a triazolinone of the formula I or an agriculturally useful salt of I, as defined in claim 1, is allowed to act on plants.

7. The triazolinone of the formula I as defined in claim 1, where $R^1$ is $C_1$–$C_6$-haloalkyl, $R^2$ is $C_1$–$C_6$-alkyl, $R^3$ is hydrogen or halogen, and $R^4$ is halogen.

8. The triazolinone of the formula I as defined in claim 1, where $R^1$ is difluoromethyl, $R^2$ is methyl, $R^3$ is halogen, $R^4$ is chlorine, and $R^5$ is chlorine or bromine.

9. The triazolinone of the formula I as defined in claim 1, where $R^3$ is fluorine.

10. The triazolinone of the formula I as defined in claim 1, where $R^1$ is difluoromethyl, $R^2$ is methyl, $R^3$ is fluorine, $R^4$ is chlorine, $R^5$ is chlorine, and $R^6$ is ethoxy.

* * * * *

UNITED STATES PATENT AND TRADEMARK OFFICE
CERTIFICATE OF CORRECTION

PATENT NO.: 5,885,934

DATED: March 23, 1999

INVENTOR(S): HEISTRACHER et al.

It is certified that error appears in the above-identified patent and that said Letters Patent is hereby corrected as shown below:

Col. 43, claim 1, line 66, "$C_1$-$C_1$-$C_6$-haloalkoxy" should be --$C_1$-$C_6$-haloalkoxy--.

Signed and Sealed this

Thirteenth Day of July, 1999

Attest:

Q. TODD DICKINSON

*Attesting Officer*

*Acting Commissioner of Patents and Trademarks*